US011219421B2

(12) United States Patent
Sugihara et al.

(10) Patent No.: US 11,219,421 B2
(45) Date of Patent: Jan. 11, 2022

(54) X-RAY CT IMAGING APPARATUS

(71) Applicant: J. MORITA MANUFACTURING CORPORATION, Kyoto (JP)

(72) Inventors: Yoshito Sugihara, Kyoto (JP); Tomoyuki Sadakane, Kyoto (JP); Masanori Otsuka, Kyoto (JP); Takahiro Yoshimura, Kyoto (JP); Yutaka Ito, Kyoto (JP); Sho Matsushita, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 56 days.

(21) Appl. No.: 16/909,985

(22) Filed: Jun. 23, 2020

(65) Prior Publication Data

US 2020/0315555 A1 Oct. 8, 2020

Related U.S. Application Data

(63) Continuation of application No. PCT/JP2018/048097, filed on Dec. 27, 2018.

(30) Foreign Application Priority Data

Dec. 28, 2017 (JP) .............................. JP2017-252968

(51) Int. Cl.
*A61B 6/00* (2006.01)
*A61B 6/14* (2006.01)
(Continued)

(52) U.S. Cl.
CPC .............. *A61B 6/14* (2013.01); *A61B 6/035* (2013.01); *A61B 6/0487* (2020.08); *A61B 6/4452* (2013.01); *A61B 6/541* (2013.01)

(58) Field of Classification Search
CPC ......... A61B 6/035; A61B 6/14; A61B 6/4435; A61B 6/03; A61B 6/027; A61B 6/589; A61B 6/547

See application file for complete search history.

(56) References Cited

U.S. PATENT DOCUMENTS

2005/0117693 A1*  6/2005  Miyano ................ A61B 6/0478
                                                                    378/4
2007/0041491 A1    2/2007  Sadakane et al.
2016/0206275 A1    7/2016  Jouhikainen

FOREIGN PATENT DOCUMENTS

EP        2198783 A1    6/2010
JP     S60-103942 A     6/1985
(Continued)

OTHER PUBLICATIONS

The Preliminary Report on Patentability (with Written Opinion) from the corresponding International Patent Application No. PCT/JP2018/048097 dated Jun. 30, 2020.
(Continued)

*Primary Examiner* — Dani Fox
(74) *Attorney, Agent, or Firm* — Shinjyu Global IP

(57) ABSTRACT

An X-ray CT imaging apparatus includes: a supporter that is supported such that an X-ray generator and an X-ray detector are opposed to each other; a turning motor that turns the supporter about a shaft; a crosswise drive motor that moves the shaft in a crosswise direction; and a circuit that performs processing of controlling the turning motor and the crosswise drive motor and processing of setting the physique of a subject. When X-ray CT imaging is performed, the crosswise drive motor moves the shaft in synchronization with turning of the supporter about the shaft, and the supporter is caused to perform combined motion, which allows the X-ray generator and the X-ray detector to turn about a center of an X-ray CT imaging region, and position control of the shaft is performed according to the size of the physique of the subject.

18 Claims, 21 Drawing Sheets

(51) Int. Cl.
*A61B 6/04* (2006.01)
*A61B 6/03* (2006.01)

(56) References Cited

FOREIGN PATENT DOCUMENTS

| | | |
|---|---|---|
| JP | H9-122118 A | 5/1997 |
| JP | 2003-290220 A | 10/2003 |
| JP | 2007-029168 A | 2/2007 |
| JP | 2009-131656 A | 6/2009 |
| JP | 2013-135842 A | 7/2013 |
| JP | 2016-016276 A | 2/2016 |
| JP | 2017-023326 A | 2/2017 |
| JP | 2017-127627 A | 7/2017 |
| WO | 2015/156603 A1 | 10/2015 |

OTHER PUBLICATIONS

The Search Report from the corresponding European Patent Application No. 18895193.3 dated Jul. 28, 2021.
The Office Action from the corresponding Japanese Patent Application No. 2019-562152 dated Apr. 6, 2021.
The Search Report from the corresponding International Patent Application No. PCT/JP2018/048097 dated Mar. 26, 2019.

\* cited by examiner

F I G . 1
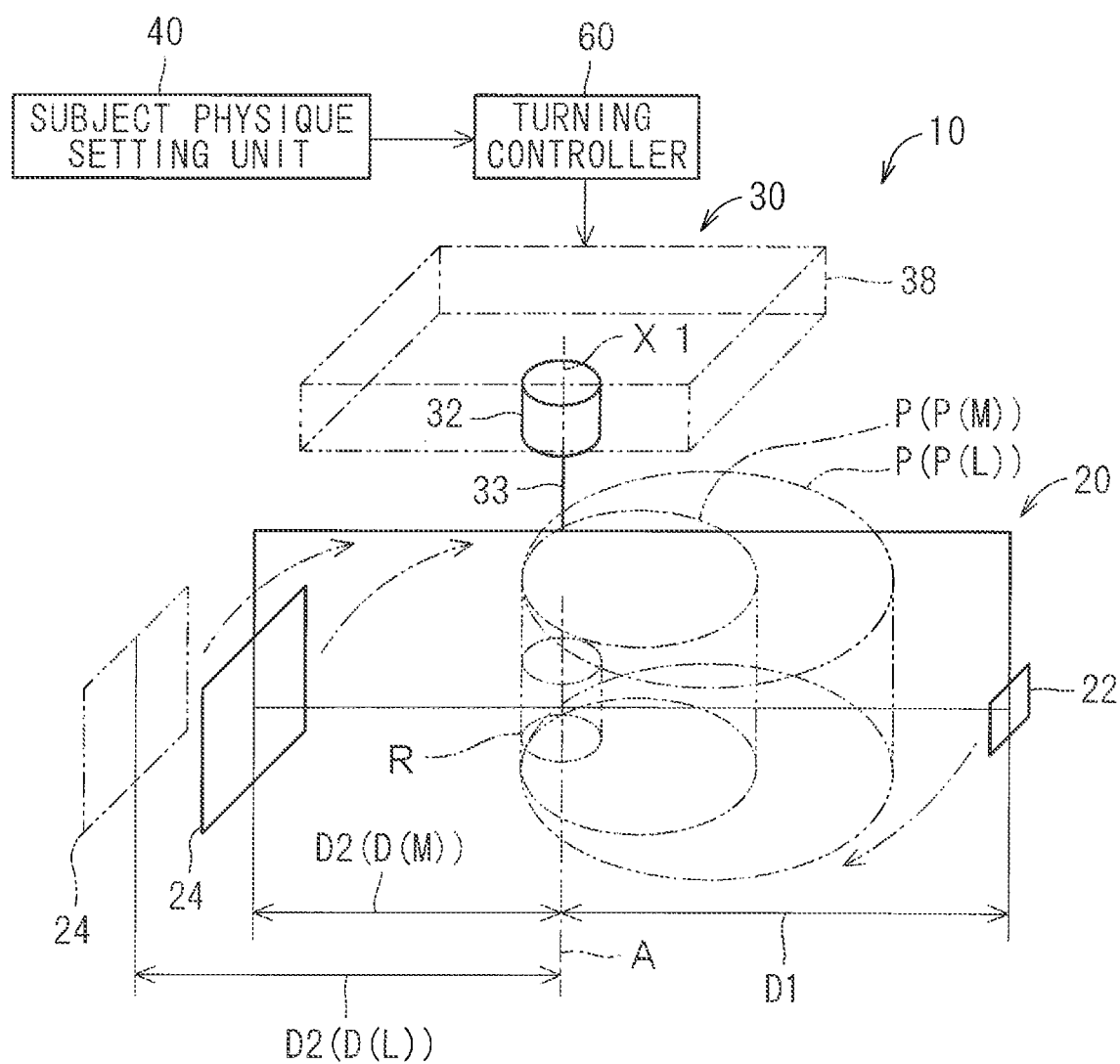

FIG. 9

| PHYSIQUE | TURNING CONTROL CONTENT | SEPARATION DISTANCE (MAGNIFICATION RATIO) | REGULATION WIDTH |
|---|---|---|---|
| P(M) | TURNING IS PERFORMED WHILE TURNING AXIS X1 IS MATCHED WITH CENTER A | D(M) m(M) | W(M) |
| P(L) | TURNING IS PERFORMED WITH RADIUS r ABOUT CENTER A | D(L) m(L) | W(L) |

F I G. 1 2
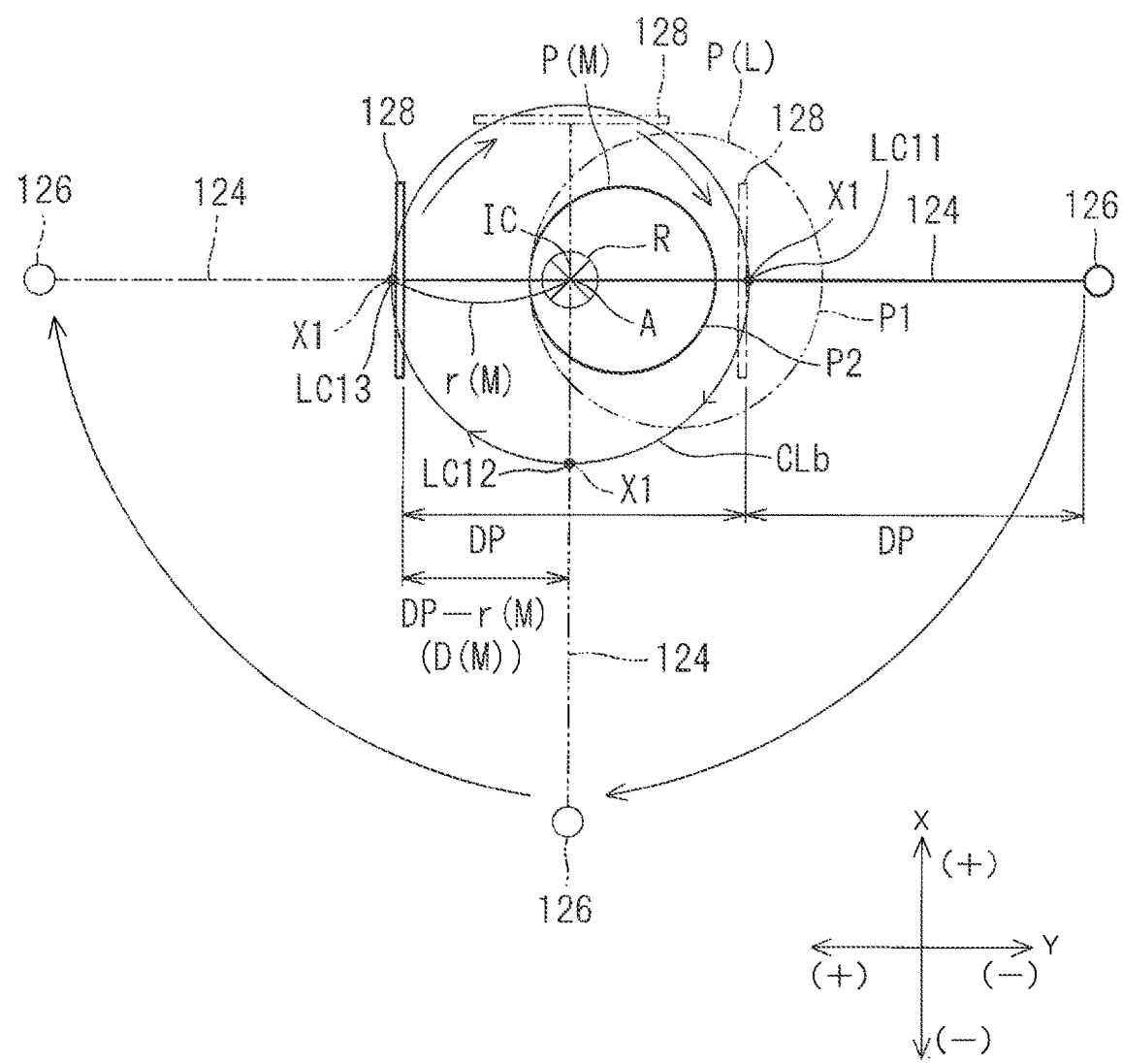

F I G . 1 9
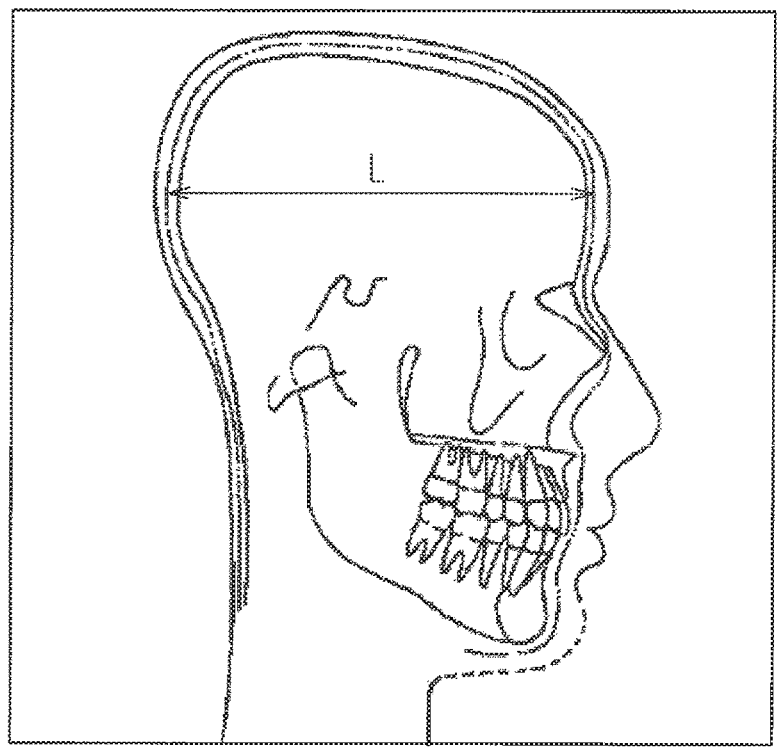
F I G . 2 0
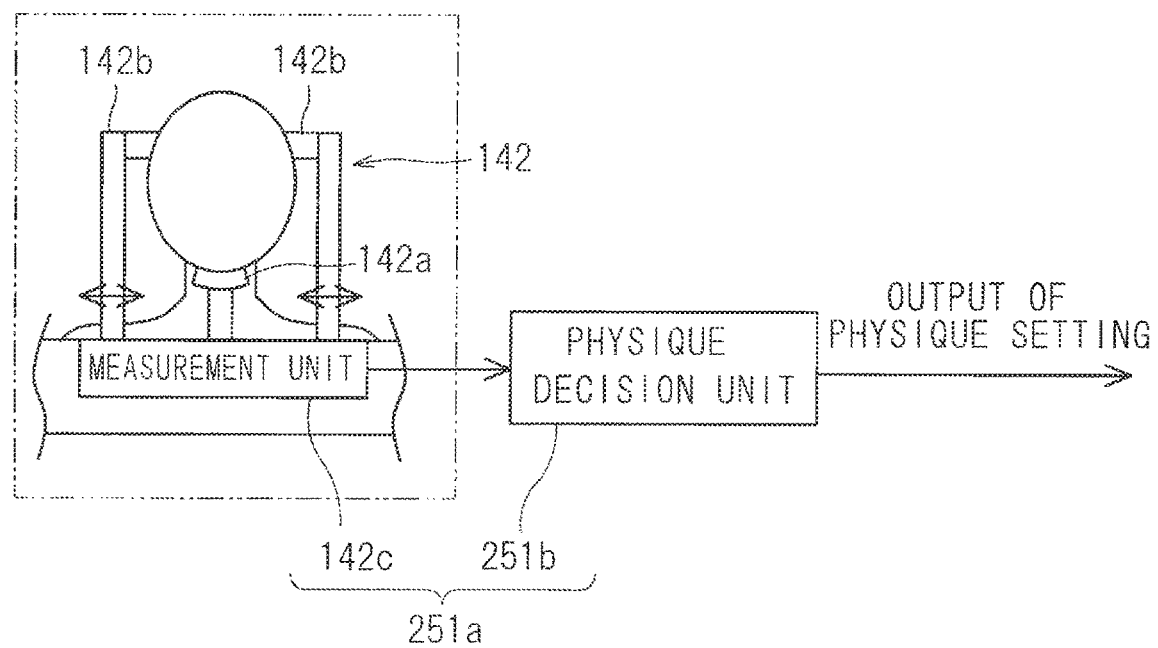

X-RAY CT IMAGING APPARATUS

CROSS-REFERENCE TO RELATED APPLICATIONS

This application is a continuation application of International Application No. PCT/JP2018/048097, filed on Dec. 27, 2018, and claims priority under 35 U.S.C. § 119 to Japanese Patent Application No. 2017-252968, filed on Dec. 28, 2017. The entire disclosures of both applications are hereby incorporated herein by reference in their entireties.

TECHNICAL FIELD

The present disclosure relates to an X-ray CT imaging apparatus that performs X-ray imaging by rotating an X-ray generator and an X-ray detector around a subject.

BACKGROUND ART

Japanese Patent Application Laid-Open No. 2007-029168 discloses an X-ray CT imaging apparatus including a turning mechanism and a moving mechanism. The turning mechanism turns turning means, in which the X-ray generator and the X-ray detector are disposed opposite to each other while the subject is sandwiched therebetween, around a turning axis. The moving mechanism moves the turning axis and/or the subject in a plane perpendicular to the turning axis. In the X-ray CT imaging apparatus, the turning means is turned by combined motion of the turning of the turning unit and the turning axis and/or the movement of the subject while a center of a region of interest of the subject is always set to a rotation center on the imaging different from the turning axis of the turning mechanism. Consequently, a magnification ratio can be changed by relatively changing a distance between the X-ray generator and the rotation center and/or a distance between the X-ray detector and the rotation center.

BRIEF SUMMARY

The subject of X-ray imaging has various sizes.

In Japanese Patent Application Laid-Open No. 2007-029168, because the size of the subject is not taken into consideration, there is a possibility that the X-ray generator and the X-ray detector turning around the subject contact with the subject.

An object of the present disclosure is to prevent the X-ray generator and the X-ray detector that turn around the subject from contacting with the subject.

An X-ray CT imaging apparatus according to one aspect includes: a supporter that is supported such that an X-ray generator and an X-ray detector are opposed to each other with a subject sandwiched between the X-ray generator and the X-ray detector; a turning motor that turns the supporter about a shaft located between the X-ray generator and the X-ray detector; a crosswise drive motor that moves the shaft in a crosswise direction, a direction parallel to an axial direction of the shaft being set to a longitudinal direction, a direction intersecting with the longitudinal direction being set to the crosswise direction; and a circuit that performs processing of controlling the turning motor and the crosswise drive motor and processing of setting a physique of the subject from physique data of the subject. When X-ray CT imaging is performed by irradiating the subject with an X-ray generated from the X-ray generator, the crosswise drive motor moves the shaft in synchronization with turning of the supporter about the shaft using the turning motor, and the supporter is caused to perform combined motion, which allows the X-ray generator and the X-ray detector to turn about a center of an X-ray CT imaging region, and position control of the shaft is performed according to a size of the physique of the subject.

BRIEF DESCRIPTION OF DRAWINGS

FIG. 1 is a schematic diagram illustrating an X-ray CT imaging apparatus according to a first embodiment.

FIG. 9 is a view illustrating an example of a reference table.

FIG. 12 is a view illustrating a turning action example when the physique is relatively small in a first modification.

FIG. 19 is a view illustrating a captured image example recognizing the physique of a subject.

FIG. 20 is a block diagram of a fifth modification.

DETAILED DESCRIPTION

First Embodiment

Figure 2:
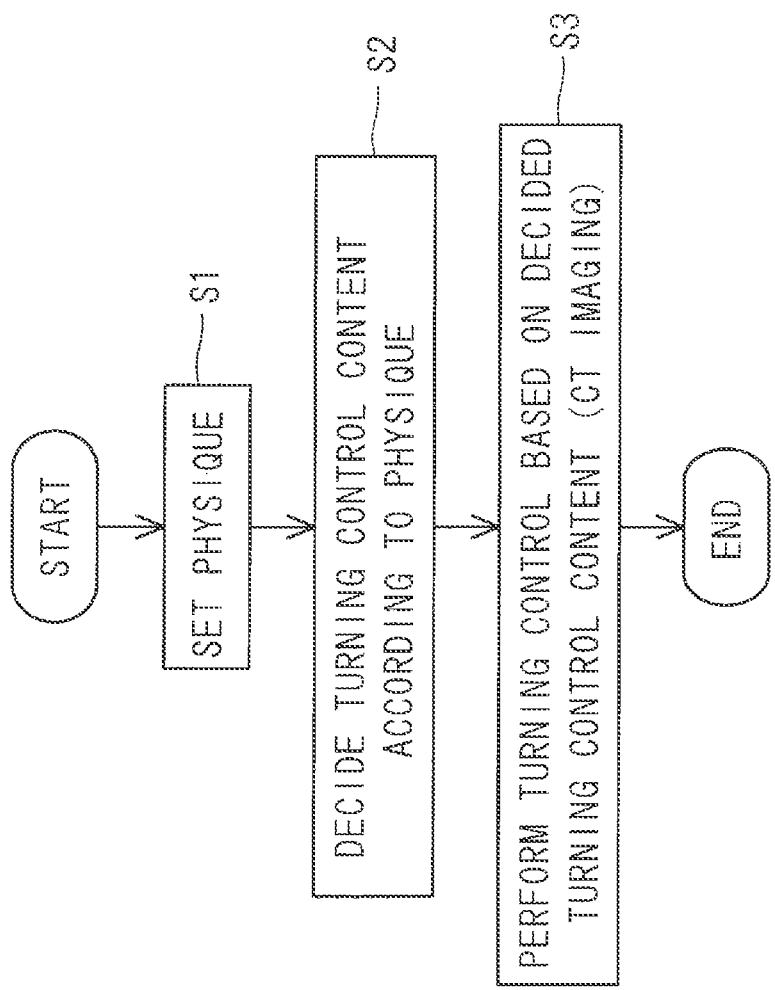
FIG. 2 is a flowchart illustrating an example of processing performed by a turning controller.

A medical X-ray CT imaging apparatus according to a first embodiment will be described below. FIG. 1 is a schematic diagram illustrating an X-ray CT imaging apparatus 10.

The X-ray CT imaging apparatus 10 is an apparatus that performs X-ray computed tomography (CT) imaging of a subject P, and includes a turning support 20, a turning drive mechanism 30, a subject physique setting unit 40, and a turning controller 60.

The turning support 20 supports an X-ray generator 22 and an X-ray detector 24 such that the X-ray generator 22 and the X-ray detector 24 are opposed to each other with a subject P sandwiched therebetween. The turning support 20 can be called a supporter that supports the X-ray generator 22 and the X-ray detector 24. The X-ray generator 22 generates an X-ray (X-ray beam). The X-ray detector 24 detects the X-ray emitted from the X-ray generator 22. The X-ray generator 22 and the X-ray detector 24 are supported by the turning support 20 while a space where the subject P is disposed between the X-ray generator 22 and the X-ray detector 24 is provided. The X-ray emitted from the X-ray generator 22 is incident on the X-ray detector 24 through the subject P. The X-ray incident on the X-ray detector 24 is converted into an electric signal corresponding to intensity of the X-ray in each unit pixel. The X-ray CT image or the like is generated based on each electric signal.

The turning drive mechanism 30 includes a turning mechanism 32 and a turning axis moving mechanism 38.

The turning mechanism 32 turns the turning support 20 about a mechanical turning axis X1 located between the X-ray generator 22 and the X-ray detector 24. An example of the mechanical turning axis X1 is an axis of a shaft about which the turning support 20 turns. In this case, it can be said that the turning mechanism 32 turns about the shaft. For example, the turning mechanism 32 includes an electric motor, and includes an acceleration and deceleration mechanism such as a gear as necessary. The turning mechanism 32 rotatably supports a shaft 33 protruding from the turning support 20 at a position between the X-ray generator 22 and the X-ray detector 24. The shaft 33 is an example of the shaft. A center axis of the shaft 33 constitutes the mechanical turning axis X1. The turning support 20 turns about the mechanical turning axis X1 by driving the turning mechanism 32. The turning mechanism 32 can have any configuration as long as the turning mechanism 32 turns the turning support 20 about the mechanical turning axis X1.

The turning axis moving mechanism 38 moves the mechanical turning axis X1 in a direction intersecting with the mechanical turning axis X1. For example, the turning axis moving mechanism 38 is constructed with an XY-stage mechanism and the like. The XY-stage mechanism is a combination of two sets of linear actuators with moving directions of the linear actuators intersecting with each other. A linear moving mechanism in which a linear guide and a ball screw feed mechanism are combined, a linear motor, and a linear motor such as an air cylinder can be used as the linear actuator. The moving direction of each of the two sets of linear actuators of the XY-stage mechanism is set to intersect with the mechanical turning axis X1, and the turning mechanism 32 is supported so as to be able to be moved in the moving direction of each of the two sets of linear actuators. Consequently, the turning mechanism 32 can be moved along a plane intersecting with the mechanical turning axis X1, and therefore the mechanical turning axis X1 can be moved along the plane intersecting with the mechanical turning axis X1.

The turning axis moving mechanism 38 is not limited to the above example, but any turning axis moving mechanism that moves the mechanical turning axis X1 in the direction intersecting with the mechanical turning axis X1 can be used.

In the X-ray CT imaging apparatus 10, in performing the X-ray CT imaging in which the subject P is irradiated with the X-rays generated from the X-ray generator 22, the turning axis moving mechanism 38 moves the mechanical turning axis X1 in synchronization with the turning of the turning support 20 about the mechanical turning axis X1 using the turning mechanism 32, and the turning support 20 is caused to perform combined motion, which allows the X-ray generator 22 and the X-ray detector 24 to be turned around the center of an X-ray CT imaging region R. The case that the X-ray generator 22 and the X-ray detector 24 are turned around a center A of the imaging region R includes the case that the X-ray generator 22 and the X-ray detector 24 are turned while drawing a circular trajectory around the center A and the case that the X-ray generator 22 and the X-ray detector 24 are turned while drawing a trajectory other than a circle.

The subject physique setting unit 40 is configured to be able to set the size of the physique of the subject P. The size of the physique of the subject P is set to the turning controller 60. Information that becomes a base in setting the size of the physique of the subject P using the subject physique setting unit 40 can be obtained by receiving an input operation performed by an operator of the X-ray CT imaging apparatus 10. Alternatively, the information can be transmission X-ray image data obtained by previously imaging the subject P using the X-ray generator 22 and the X-ray detector 24. Alternatively, the information can be visible light image data obtained by imaging the subject P using an imager such as a CCD camera. Alternatively, the information can be data based on a signal output from a sensor or the like provided in the subject holder holding the subject P. That is, information input after a judgment by a person, data based on output signals of various sensors that output signals according to the physique of the subject P, and the like can be used as the above information, and the subject physique setting unit 40 sets the size of the physique of the subject P based on the information.

The turning controller 60 controls the turning mechanism 32 and the turning axis moving mechanism 38. In particular, the turning controller 60 performs position control of the turning axis X1 according to a size of the physique of the subject P set by the subject physique setting unit 40.

The turning controller 60 includes at least one processor. For example, the turning controller 60 is constructed with a computer including at least one processor, a Random Access Memory (RAM), a storage, and an input and output unit. The storage is constructed with a flash memory or a nonvolatile storage device such as a hard disk drive, and stores a turning control program in controlling the turning mechanism 32 and the turning axis moving mechanism 38. The RAM serves as a work area when at least one processor performs predetermined processing. The input and output unit is connected to the turning mechanism 32, the turning axis moving mechanism 38, the subject physique setting unit 40, and the like. Then, at least one processor performs predetermined arithmetic processing according to the turning control program stored in the storage, and controls the turning mechanism 32 and the turning axis moving mechanism 38 according to the set physique of the subject P. Because the processor and the RAM include a circuit or are connected to each other by a circuit, the turning controller 60 is an element mechanically constructed with a circuit. The turning controller 60 is a circuit that mechanically processes the turning control according to a program. Similarly, the subject physique setting unit 40 is a circuit that performs processing of setting the physique of the subject from physique data of the subject according to the program.

FIG. 2 is a flowchart illustrating processing performed by the turning controller 60.

That is, in step S1, the physique of the subject P is set in performing the X-ray CT imaging.

In step S2, a turning control content according to the size of the physique of the subject P is decided.

The turning control content includes information about position control such as how to control the position of the mechanical turning axis X1 in turning the X-ray generator 22 and the X-ray detector 24 around the center of the X-ray CT imaging region R. The following example can be considered as an example of the position control of the mechanical turning axis X1. In the first position control example, the turning axis moving mechanism 38 moves the mechanical turning axis X1 in synchronization with the turning of the turning support 20 about the mechanical turning axis X1 using the turning mechanism 32. In this case, the turning axis moving mechanism 38 can turn the mechanical turning axis X1 around the X-ray CT imaging region R in synchronization with the turning of the turning support 20 about the mechanical turning axis X1 using the turning mechanism 32. At this point, the turning axis moving mechanism 38 can rotate the mechanical turning axis X1 with the center A of the X-ray CT imaging region R as the rotation center. In the second position control example, the mechanical turning axis X1 is fixed to the center A of the X-ray CT imaging region R when the turning mechanism 32 turns the turning support 20 about the mechanical turning axis X1.

By switching the position control of the mechanical turning axis X1 between the first position control example and the second position control example, the trajectory along which the X-ray generator 22 and the X-ray detector 24 turn can be changed so as to be moved away from or brought close to the X-ray CT imaging region R. Alternatively, by changing the position (distance) of the mechanical turning axis X1 to the center A of the X-ray CT imaging region R, the trajectory along which the X-ray generator 22 and the X-ray detector 24 turn can be changed so as to be moved away from or brought close to the X-ray CT imaging region R. These position control examples are more specifically described in a second embodiment.

By combining the position control examples, the trajectory along which the X-ray generator 22 and the X-ray detector 24 turn can be changed in multiple stages so as to be moved away from or brought close to the X-ray CT imaging region R.

The X-ray CT imaging region R is a region that is set as a target of the X-ray CT imaging in the subject P. The X-ray CT imaging region R can be a whole or a part of the subject P. The X-ray CT imaging region R can be a previously-defined region as a predetermined region of the subject P, or a region set by the operator or the like each time the CT imaging is performed. Hereinafter, sometimes the X-ray CT imaging region R is simply referred to as an imaging region R.

As described above, when the X-ray generator 22 and the X-ray detector 24 are turned around the center A of the imaging region R, the turning axis moving mechanism 38 controls the position of the mechanical turning axis X1 with respect to the center A of the imaging region R according to the size of the physique.

As an example, it is assumed that D1 is a distance between the center A of the imaging region R and the X-ray generator 22, that D2 is a distance between the center A of the imaging region R and the X-ray detector 24, and that a separation distance D is a smaller one of the two distances D1, D2. The case that the physique of the subject P set by the subject physique setting unit 40 is a first physique P(L) and the case that the physique of the subject P is a second physique P(M) smaller than the first physical constitution P(L) are assumed. The position of the mechanical turning axis X1 is controlled such that the separation distance D when the set physique of the subject P is the relatively large first physique P(L) is greater than the separation distance D when the set physique of the subject P is the relatively small second physique P(M) according to the size of the physique of the subject P set by the subject physique setting unit 40.

When the size in FIG. 1 is described as an example, because the center A of the imaging region R is located closer to the X-ray detector 24 than the X-ray generator 22, the separation distance D is the distance D2 between the center A of the imaging region R and the X-ray detector 24. Assuming that the position control of the mechanical turning axis X1 is performed according to the size of the physique, the separation distance for the relatively large first physique P(L) is set to D(L), and the relatively small second physique P(M) is set to D(M). In this case, the separation distance D(L) for the relatively large first physique is increased larger than the separation distance D(M). When the separation distance D(L) is increased, the X-ray generator 22 approaches the center A of the imaging region R, but it is assumed that the separation distance D(L) is set to a range less than or equal to D1 of the adjusted distance, namely, a range in which the X-ray generator 22 is not brought closer to the center A of the imaging region R than the X-ray detector 24.

For the relatively small second physique P(M), the X-ray detector 24 is turned with a radius corresponding to the relatively small separation distance D(M). For this reason, the X-ray detector 24 can be turned while brought as close as possible to the second physique P(M). The X-ray generator 22 turns a position farther from the center A of the imaging region R than the X-ray detector 24, namely, the X-ray generator 22 turns such that a degree of separation with respect to the center A is larger than a degree of separation with respect to the center A of the X-ray detector 24.

For the relatively large first physique P(L), the X-ray detector 24 is turned with a radius corresponding to the relatively large separation distance D(L). Consequently, the X-ray detector 24 can be turned without interfering with the first physique P(L). The X-ray generator 22 turns a position farther from the center A of the imaging region R than the X-ray detector 24, namely, the X-ray generator 22 turns such that a degree of separation with respect to the center A is larger than a degree of separation with respect to the center A of the X-ray detector 24.

For example, the turning control content of the mechanical turning axis X1 according to the size of the physique can be decided by referring to the reference table previously stored in the storage according to the set sizes of a plurality of physiques. For example, the reference table can be set to a table in which the turning control content of the turning axis X1 is associated with each of the plurality of physiques.

When the second position control example is assumed, the turning control content is defined as fixing of the mechanical turning axis X1 to a fixed position. When the first position control example is assumed, the turning control content is defined as a pattern moving the mechanical turning axis X1 around the center A of the imaging region R. A more specific example is a pattern in which the mechanical turning axis X1 is rotated with a predetermined axis turning radius as the center A of the imaging region R as a rotation center. The predetermined axis turning radius can be a value previously set according to the size of the physique. The turning control content (for example, the predetermined axis turning radius) can be obtained each time by calculation using a previously-set arithmetic expression or the like according to the value representing the set sizes of the plurality of physiques. Consequently, the turning control content including the position control of the turning axis X1 is decided.

In step S3, the turning controller 60 controls the turning mechanism 32 and the turning axis moving mechanism 38 based on the decided turning control content, and the X-ray generator 22 and the X-ray detector 24 are turned around the center A of the imaging region R of the subject P. At this point, the X-rays emitted from the X-ray generator 22 is incident on the X-ray detector 24 through the subject P, and data used to generate the X-ray CT image is obtained. The X-ray CT image is generated based on this data.

In the X-ray CT imaging apparatus 10 configured as described above, the position control of the turning axis X1 is performed according to the size of the physique of the subject P set by the subject physique setting unit 40, so that the X-ray generator 22 and the X-ray detector 24 that turn around the subject P can be prevented from contacting with the subject P by changing the turning orbits of the X-ray generator 22 and the X-ray detector 24.

The position control of the turning axis X1 is performed according to the size of the physique of the subject P to change the turning orbits of the X-ray generator 22 and the X-ray detector 24, so that the X-ray CT imaging can be performed by bringing the X-ray detector 24 as close as possible to the subject P while the contact of the X-ray detector 24 with the subject P is prevented. Consequently, the clear X-ray image can be generated.

Second Embodiment

An X-ray CT imaging apparatus according to a second embodiment will be described.

<Entire Configuration>

Figure 3:
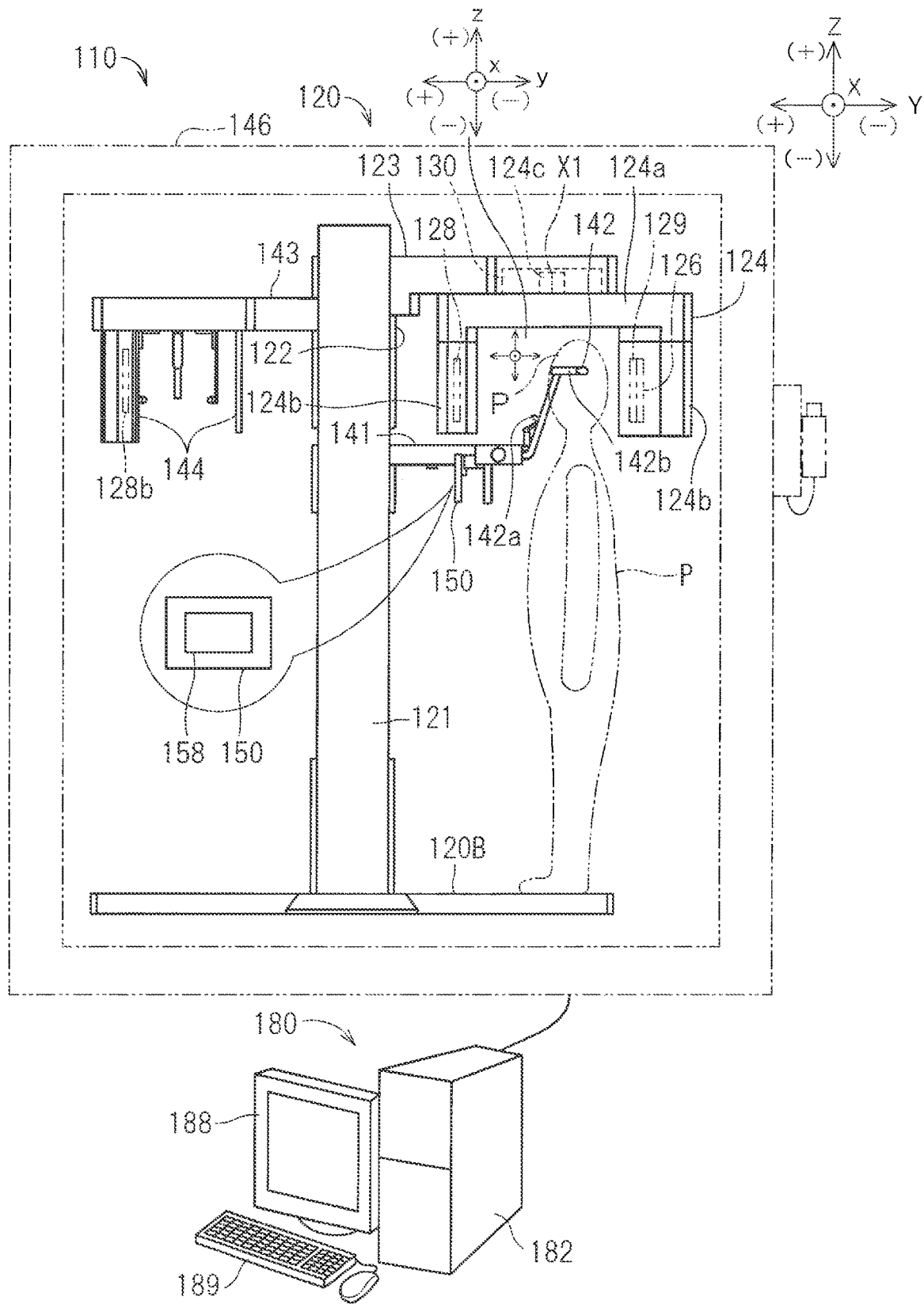
FIG. 3 is a schematic diagram illustrating an entire configuration of an X-ray CT imaging apparatus according to a second embodiment.

FIG. 3 is a schematic diagram illustrating an entire configuration of an X-ray CT imaging apparatus 110. An example in which the X-ray CT imaging apparatus 110 can perform not only the X-ray CT imaging but also panoramic imaging, cephalogram imaging, and the like will be described. An example in which the subject of the X-ray CT imaging apparatus 110 is the head P of a human body will be described.

The X-ray CT imaging apparatus 110 includes an imaging main body 120 and an X-ray image processing apparatus 180. The imaging main body 120 is an apparatus that performs the X-ray imaging such as the X-ray CT imaging to collect projection data. The X-ray image processing apparatus 180 is an apparatus that processes the projection data collected by the imaging main body 120 and generates various images.

The imaging main body 120 includes a turning support 124 and a turning drive mechanism 130. The turning support 124 supports an X-ray generator 126 and an X-ray detector 128 such that the X-ray generator 126 and the X-ray detector 128 are opposed to each other with the head P sandwiched therebetween. The turning support 124 can be called a supporter that supports the X-ray generator 126 and the X-ray detector 128. The turning drive mechanism 130 includes a turning mechanism 132 and a turning axis moving mechanism 134. The turning mechanism 132 is a mechanism that turns the turning support 124 about the mechanical turning axis X1 between the X-ray generator 126 and the X-ray detector 128. The turning axis moving mechanism 134 is a mechanism that moves the mechanical turning axis X1 in a direction intersecting with the mechanical turning axis X1. An example of the mechanical turning axis X1 is an axis of a shaft about which the turning support 20 turns. In this case, it can be said that the turning mechanism 32 turns about the shaft.

More specifically, a post 121 is supported in a perpendicular posture on a base 120B. A lifting unit 122 is liftably provided on the post 121. A lifting drive mechanism moves the lifting unit 122 up and down. A moving mechanism including a ball screw mechanism and a motor and a linear actuator such as a linear motor are used as the lifting drive mechanism, and the lifting drive mechanism moves the lifting unit 122 up and down while being incorporated in the post 121. A horizontal arm 123 is supported by the lifting unit 122 so as to extend in a horizontal direction. A turning drive mechanism 130 is incorporated at a leading end of the horizontal arm 123. A head fixing apparatus arm 141 (to be described later) extends from the post 121 in the same direction as the horizontal arm 123. A head fixing apparatus 142 is provided at the leading end of the head fixing apparatus arm 141, and the head P is held by the head fixing apparatus 142. In FIG. 3, a base end of the lifting unit 122 moves up and down behind the post 121. Assuming that the side on which the base end of the lifting unit 122 moves up and down is a back face and that a reverse of the back face is a front face, the horizontal arm 123 extends from the lifting unit 122 to the right of the post 121 in front view of FIG. 3. The head P is held in the head fixing apparatus 142 with the right in FIG. 3 as the rear and with the left as the front.

At this point, the direction is defined for convenience.

An XYZ-orthogonal coordinate system is an orthogonal coordinate system defined in a three-dimensional space in which the imaging main body 120 is installed. A direction parallel to the axial direction of the mechanical turning axis X1 is set to a Z-axis direction. In the second embodiment, the direction parallel to the axial direction of the mechanical turning axis X1 and the lifting direction of the lifting unit 122 are matched with each other as the Z-axis direction. A direction orthogonal to the Z-axis direction is set to a Y-axis direction, and a direction orthogonal to the Z-axis direction and the Y-axis direction is set to an X-axis direction. A front-rear direction of the head P fixed to the head fixing apparatus 142 is set to the Y-axis direction, and a right and left direction of the head P is set to the X-axis direction.

In the present disclosure, sometimes the Z-axis direction is referred to as a Z-direction, the Y-axis direction is referred to as a Y-direction, and the X-axis direction is referred to as an X-direction. The Z-axis direction can be considered as a longitudinal direction, and the X-direction and the Y-direction can also be considered as a crosswise direction. The longitudinal direction can be a vertical direction, and the Y-direction can be a horizontal direction.

The direction from the head P toward the base 120B, namely, a lower side is set to a −Z-side, and the direction away from the base 120B from the head P, namely, an upper side is set to a +Z-side. The front side of the head P is set to a +Y-side, and the rear side is set to a −Y-side. The right side of the head P is set to an +X-side, and the left side is set to an −X-side. Each axial direction, "+", and "−" are illustrated in FIG. 3.

An xyz-orthogonal coordinate system is an orthogonal coordinate system defined in the turning support 124 constituting an imaging system that performs the X-ray generation and the X-ray detection, the imaging system rotating around the mechanical turning axis X1. At this point, the axial direction of the mechanical turning axis X1 is set to a z-axis direction, and the z-axis direction is matched with the Z-axis direction of the XYZ-orthogonal coordinate system. A direction in which the X-ray generator 126 and the X-ray detector 128 are opposed to each other is set to a y-axis direction, and a direction orthogonal to the y-axis direction and the z-axis direction is set to an x-axis direction. The turning support 124 rotates with the mechanical turning axis X1 as the rotation axis, which allows the xyz-orthogonal coordinate system to rotate around the Z-axis (=z-axis) with respect to the XYZ-orthogonal coordinate system. In the present disclosure, sometimes the z-axis direction is referred to as a z-direction, the y-axis direction is referred to as a y-direction, and the x-axis direction is referred to as an x-direction.

In the y-axis direction, the side of the X-ray detector 128 is set to a +y-side, and the side of the X-ray generator 126 is set to a −y-side. In the x-axis direction, the right side from the −y-side toward the +y-side is set to a +x-side, and the left side is set to a −x-side. In the z-axis direction, the upper side in the vertical direction is set to a +z-side, and the lower side is set to a −z-side.

Figure 4:
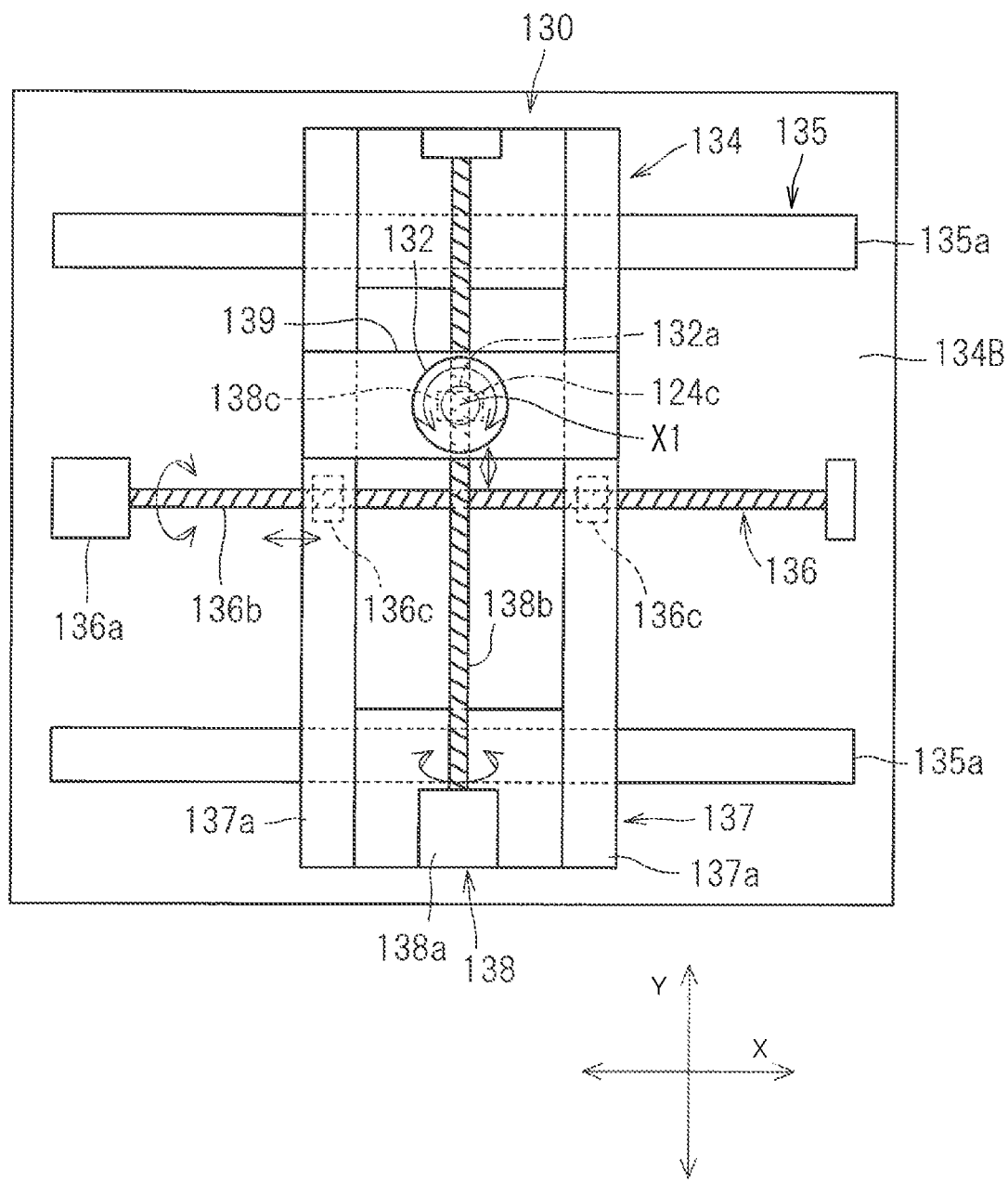
FIG. 4 is a schematic bottom view illustrating a turning axis moving mechanism.

FIG. 4 is a schematic bottom view illustrating the turning drive mechanism 130. As illustrated in FIGS. 3 and 4, the turning drive mechanism 130 includes a turning axis moving mechanism 134 supported by the horizontal arm 123 as a kind of bracket and a turning mechanism 132 supported movably by the turning axis moving mechanism 134.

The turning axis moving mechanism 134 is a mechanism that moves the mechanical turning axis X1 in the direction intersecting with the mechanical turning axis X1, in this case, the direction orthogonal to the mechanical turning axis X1. The turning axis moving mechanism 134 is constructed with an XY-table mechanism, and the mechanical turning axis X1 is moved in the direction intersecting with the mechanical turning axis X1 by moving the turning mechanism 132 to which the mechanical turning axis X1 is connected in the direction intersecting withe the mechanical turning axis X1. More specifically, the turning axis moving mechanism 134 includes a fixed table 134B, an X-direction movable support 135, an X-direction drive unit 136, a Y-direction movable support 137, a Y-direction drive unit 138, and a movable table 139.

The X-direction movable support 135 includes a pair of linear guides 135a extending in the X-direction, the linear guides 135a being supported on the fixed table 134B in a spaced and parallel state. The Y-direction movable support 137 includes a pair of linear guides 137a extending in the Y-direction. The pair of linear guides 137a are movably supported on the pair of linear guides 135a along the X-direction that is the extending direction while having a posture intersecting with the pair of linear guides 135a (in this case, a posture orthogonal to the pair of linear guides 135a) in the spaced and parallel state. The movable table 139 is supported on the pair of linear guides 137a so as to be movable along the Y-direction that is the extending direction. The Y-direction movable support 137 moves along the X-direction on the X-direction movable support 135, which allows the movable table 139 to move in the X-direction. The movable table 139 moves along the Y-direction on the Y-direction movable support 137, which allows the movable table 139 to move in the Y-direction. Consequently, the movable table 139 can move freely in a plane orthogonal to the mechanical turning axis X1.

The X-direction drive unit 136 is a mechanism that reciprocally drives the Y-direction movable support 137 along the X-direction. For example, a ball screw mechanism in which a nut 136c fixed to the Y-direction movable support 137 is screwed to a ball screw 136b rotationally driven in both forward and reverse directions by a motor 136a can be used as the X-direction drive unit 136.

The Y-direction drive unit 138 is a mechanism that reciprocally drive the movable table 139 along the Y-direction. For example, a ball screw mechanism in which a nut 138c fixed to the movable table 139 is screwed to a ball screw 138b rotationally driven in both the forward and reverse directions by a motor 138a can be used as the Y-direction drive unit 138.

The turning mechanism 132 includes a motor 132a, and is supported in a suspended state by the movable table 139. A shaft 124c protruding upward from an intermediate portion in the extending direction of the turning support 124 is supported in the suspended state by the turning mechanism 132. The shaft 124c is an example of the shaft. The rotating movement of the motor 132a is transmitted to the shaft 124c, and the turning support 124 is turned about the shaft 124c by driving the motor 132a. The central axis of the shaft 124c is the mechanical turning axis X1 located between the X-ray generator 126 and the X-ray detector 128. The rotating movement of the motor 132a is transmitted to the shaft 124c through a transmission mechanism such as a gear and a pulley as necessary. The shaft 124c is disposed along the vertical direction along a direction of gravity. Thus, the mechanical turning axis X1 is also disposed along the vertical direction.

The turning mechanism 132 supported by the movable table 139 can be moved along the plane orthogonal to the mechanical turning axis X1 by driving the X-direction drive unit 136 and the Y-direction drive unit 138. In particular, by combining the drive in the X-direction by the X-direction drive unit 136 and the drive in the Y-direction by the Y-direction drive unit 138, the turning mechanism 132 can be rotationally moved so as to draw an arc-shaped orbit.

The mechanism that moves the movable table 139 in the X-direction and the mechanism that moves the movable table 139 in the Y-direction are not limited to the above examples, but a configuration using a linear actuator such as a linear motor can be adopted. The turning axis moving mechanism 134 does not necessarily have the above configuration. The turning axis moving mechanism can be a mechanism that moves the turning mechanism only along one linear direction intersecting with the mechanical turning axis X1. The turning axis moving mechanism can be a mechanism, such as a robot arm including a plurality of joints, which turns an arm supporting the turning mechanism, thereby turning the turning mechanism in the direction intersecting with the mechanical turning axis X1. The turning axis moving mechanism 134 can move the mechanical turning axis X1 in a two-dimensional direction intersecting with the axial direction of the mechanical turning axis X1. The intersection can be orthogonal intersection.

The motor 132a is a turning motor. When the axis of the shaft is assumed as the mechanical turning axis X1, the motor 136a and the motor 138a are a crosswise drive motor that laterally moves the shaft by laterally moving the turning mechanism 132. The shaft in which the axis is the mechanical turning axis X1 is fixed to the turning support 124, and the motor 132a turns the shaft to turn the turning support 124. A drive source that moves the mechanical turning axis X1 in the lateral two-dimensional direction can be considered as a lateral drive actuator, and can be referred to as a lateral drive driver. The set of the motor 136a and the motor 138a can be considered as an example of a lateral drive actuator. When the lateral direction is the horizontal direction, the lateral drive actuator can be referred to as a horizontal drive actuator. The horizontal drive actuator can be restated for a horizontal driver.

The turning mechanism can be provided in the turning support. For example, the turning axis moving mechanism can directly move the mechanical turning axis X1 with no use of the turning mechanism. As a more specific example, a shaft corresponding to the mechanical turning axis X1 is fixed to the movable table 139 so as not to be turnable and so as to be movable in the direction intersecting with the mechanical turning axis X1, and the turning support 124 is turnably connected to the shaft. The turning mechanism 132 is provided in the turning support 124, and the turning mechanism 132 generates turning force with respect to the shaft, whereby the turning support 124 can be turned with respect to the shaft. Even in this structure, the turning mechanism 132 is a mechanism that turns the turning support 124 about the mechanical turning axis X1 between the X-ray generator 126 and the X-ray detector 128.

When the X-ray CT imaging is performed by irradiating the head P that is the subject with the X-ray generated from the X-ray generator 126, the turning axis moving mechanism 134 moves the mechanical turning axis X1 in synchronization with the turning of the turning support 124 about the mechanical turning axis X1 using the turning mechanism 132, and the turning support 124 is caused to perform the combined motion, which allows the X-ray generator 126 and the X-ray detector 128 to be turned around the center of an X-ray CT imaging region R.

As illustrated in FIG. 3, the turning support 124 has a shape in which suspending supports 124b are provided at both ends of the elongated arm body 124a, namely, a U-shape that is open downward. The shaft 124c protruding upward is provided in the intermediate portion in the extending direction of the arm body 124a, and the shaft 124c is supported in the suspended state by the turning mechanism 132.

The X-ray generator 126 is provided in one suspending support 124b. The X-ray generator 126 includes an X-ray tube, and is configured to be capable of outputting the X-ray emitted from the X-ray tube toward the X-ray detector 128.

An X-ray regulating unit 129 that adjusts a regulation amount of the X-ray generated from the X-ray generator 126 is provided on the side irradiated with the X-ray with respect to the X-ray detector 128. The X-ray regulating unit 129 is a member in which an X-ray regulating hole is made. The X-ray regulating unit 129 permits passage of part of the X-ray generated from the X-ray generator 126 according to the shape and size of the X-ray regulating hole, and shields an outside of a passage range of the X-ray. The X-ray regulating unit 129 is also a shield that regulates the X-ray. Consequently, the range of the X-ray beam traveling to the X-ray detector 128 is regulated. In the X-ray regulating unit 129, a plurality of types of X-ray regulating holes are made to switch the X-ray regulating holes regulating X-rays, or a member in which the X-ray regulating hole is made is moved to adjust an opening width of the X-ray regulating hole, thereby adjusting a shielded amount of the X-ray generated from the X-ray generator 126, namely, the regulation amount.

The X-ray detector 128 is provided in one suspending support 124b. The X-ray detector 128 includes an X-ray detector including a planar detection surface, and is configured to be able to detect the X-ray (X-ray beam), which is emitted from the X-ray generator 126 and transmitted through the head P. Projection data of the X-ray imaging can be obtained by the X-ray detector 128.

A space in which the head P can be disposed is provided between the X-ray generator 126 and the X-ray detector 128.

In the second embodiment, the X-ray generator 126 and the X-ray detector 128 are attached to both ends of the U-shaped turning support. Alternatively, the X-ray generator and the X-ray detector can be supported by an annular member while opposed to each other. A shaft can be provided on a support member traversing a part in a circumferential direction or an inside of the annular member such that the annular member can turnably be supported. In the second embodiment, the X-ray generator 126 and the X-ray detector 128 are supported so as to be rotatable around the vertical axis. Alternatively, the X-ray generator 126 and the X-ray detector 128 can be supported so as to be rotatable around an axis oblique to the vertical direction.

The turning support 124 can move up and down by the lifting unit 122 according to a height of the head P. The turning support 124 can be turned by the turning drive mechanism 130 such that the X-ray generator 126 and the X-ray detector 128 turn about the head P.

The head fixing apparatus arm 141 extending in the horizontal direction is provided in a portion of the post 121 below the horizontal arm 123. The horizontal arm 123 and the head fixing apparatus arm 141 extend in the same direction with the side of the post 121 as the base end. The head fixing apparatus arm 141 extends toward the lower side of the horizontal arm 123, and the head fixing apparatus 142 is provided at a leading end of the head fixing apparatus arm 141. The head fixing apparatus 142 is located between the X-ray generator 126 and the X-ray detector 128. The head fixing apparatus 142 includes a chin rest 142a on which a chin of the head P that is the subject can be placed and supported and a head holder 142b that holds the head P that is the subject while sandwiching the head P from both outsides. The chin of the head P is supported on the chin rest 142a, and the head P is sandwiched by the head holder 142b, whereby the head P is held at a fixed position between the X-ray generator 126 and the X-ray detector 128. The head fixing apparatus 142 can be constructed with at least one of the chin rest 142a and the head holder 142b. A cephalogram imaging head fixing apparatus suspending arm 143 is provided so as to extend in the horizontal direction on the side opposite to the side on which the horizontal arm 123 extends from the post 121, and a cephalogram imaging head fixing apparatus 144 is supported in the suspended state by the cephalogram imaging head fixing apparatus suspending arm 143. A cephalogram imaging X-ray detector 128b is incorporated in the cephalogram imaging head fixing apparatus 144.

A main body controller 150 including an operation panel apparatus 158 is provided in an intermediate portion in the extending direction of the head fixing apparatus arm 141. In FIG. 3, the operation panel apparatus 158 of the main body controller 150 is enlarged and drawn in a balloon.

The X-ray imaging is performed in the state in which the head P that is the subject is fixed by the head fixing apparatus 142, and in the state in which the turning support 124 is stopped or rotated according to a desired imaging mode. Consequently, the X-ray image data necessary for the generation of the image of the X-ray CT imaging, panoramic imaging, and the like can be obtained. For example, the X-ray imaging is performed while the turning support 124 is turned, which allows the obtainment of the X-ray CT image data necessary for the generation of the X-ray CT image. In addition, panoramic photographed images can be obtained by carrying out the X-ray imaging while the turning support 124 is rotated within a certain range, which allows the obtainment of a panoramic image. Additionally, the X-ray CT imaging apparatus 110 can also perform the X-ray imaging in order to obtain the cephalogram image and a pseudo-oral image. For example, the head P is fixed to the cephalogram imaging head fixing apparatus 144 supported by the cephalogram head fixing apparatus suspending arm 143 extending horizontally from the post 121 while the turning support 124 is stopped, and the X-ray is emitted from the X-ray generator 126 to perform the X-ray imaging, which allows the cephalogram image to be obtained. A function of imaging the panoramic image and a function of imaging the cephalometric image are sometimes omitted.

The main body controller 150 is configured to be able to receive each instruction to the imaging main body 120, and is configured to be able to control each action of the imaging main body 120. The main body controller 150 is fixed to the head fixing apparatus arm 141 extending in the horizontal direction from the post 121. The operation panel apparatus 158 is provided in the main body controller 150, the operation panel apparatus 158 displaying various kinds of information from the main body controller 150 while receiving various commands to the main body controller 150. The operation panel apparatus 158 is a touch panel including a display apparatus such as a liquid crystal display panel and a touch detector disposed on a display screen of the display apparatus. A touch operation of the user on the display screen is detected with the touch detector, which allows the reception of the operation performed on the X-ray CT imaging apparatus 110. The operation panel apparatus 158 functions as a display apparatus, namely, a display as well as an operation unit that receives the operation of the operator. A push button can be provided near the operation panel apparatus 158. The display apparatus and an input apparatus (operation unit) that receives the operation of the user can separately be provided. A user interface can be used as the input apparatus that receives the operation of the operator. More specifically, a physical user interface or a speech input user interface can be used as the input apparatus.

Each unit of the imaging main body 120 is accommodated in an X-ray protection chamber 146. A push button switch called a deadman switch that issues an instruction of the X-ray irradiation to the main body controller 150 is provided on an outside of a wall of the X-ray protection chamber 146.

The X-ray image processing apparatus 180 includes an information processing main body 182 constructed with a computer or a work station, and is connected to the imaging main body 120 through a communication cable so as to be able to transmit and receive various data. However, the transmission and reception of the data can be performed by wireless communication between the imaging main body 120 and the X-ray image processing apparatus 180. The information processing main body 182 can perform various pieces of image processing based on the data transmitted from the imaging main body 120.

A display (display apparatus) 188 constructed with a display apparatus such as a liquid crystal monitor and an operation unit (input apparatus) 189 constructed with a keyboard or a mouse are connected to the X-ray image processing apparatus 180. The operator can issue various instructions to the information processing main body 182 by operating a pointer through the mouse on characters or images displayed on the display 188. The display 188 can be constructed with a touch panel.

Part or whole of the processing of the X-ray image processing apparatus 180 can be performed by the main body controller 150. Alternatively, part or whole of the processing of the main body controller 150 can be performed by the X-ray image processing apparatus 180.

<Block Diagram of X-Ray CT Imaging Apparatus>

Figure 5:
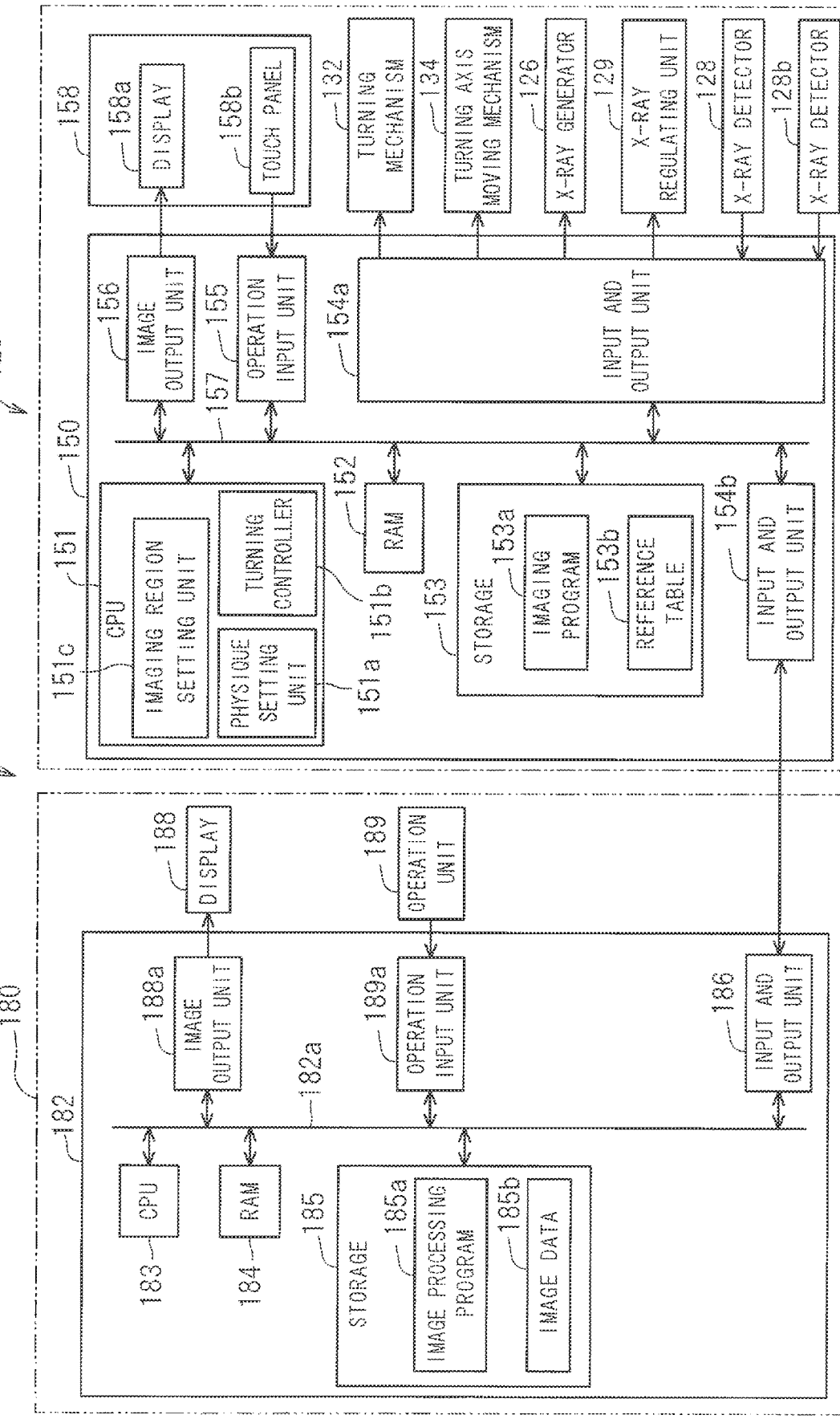
FIG. 5 is a block diagram illustrating an electric configuration of the X-ray CT imaging apparatus.

FIG. 5 is a block diagram illustrating an electric configuration of the X-ray CT imaging apparatus 110.

The main body controller 150 of the imaging main body 120 controls an X-ray imaging action of the imaging main body 120, and is constructed with a computer in which a Central Processing Unit (CPU) 151 that is at least one processor, a Random Access Memory (RAM) 152, a storage 153, input and output units 154a, 154b, an operation input unit 155, and an image output unit 156 are interconnected to one another through a bus line 157. The storage 153 includes a flash memory or a nonvolatile storage device such as a hard disk drive. An imaging program 153a, which receives various instructions relating to the X-ray imaging while controlling the X-ray imaging action by controlling the turning drive mechanism 130, the X-ray generator 126, the X-ray regulating unit 129, and the like according to the instructions, is stored in the storage 153. When the physique of the head P that is the subject is set, a reference table 153b that is referred to in deciding the turning control content of the turning drive mechanism 130 according to the set physique of the head P is stored in the storage 153. The reference table 153b is a table in which the turning control contents of the turning drive mechanism 130 and the like are correlated with the sizes of a plurality of physiques of the heads P. In consideration of the size of the physique of the head P, the distance of the X-ray generator 126 and the X-ray detector 128 to the mechanical turning axis X1, and the like, the turning control content of the turning drive mechanism 130 is theoretically and experimentally decided such that the X-ray generator 126 and the X-ray detector 128 do not contact with the head P during the turning of the X-ray generator 126 and the X-ray detector 128. An example of the turning control content according to the size of the physique of the head P will be described later. The RAM 152 serves as a work area when the CPU 151 performs predetermined processing. The input and output unit 154a is connected to a motor of the turning mechanism 132 that turns the turning support 124 of the imaging main body 120, a motor of the turning axis moving mechanism 134 that moves the turning support 124, the X-ray generator 126, the X-ray detectors 128, 128b, and the X-ray regulating unit 129, and the input and output unit 154b is communicably connected to the X-ray image processing apparatus 180. The operation input unit 155 is connected to the touch detector 158b of the operation panel apparatus 158, and the image output unit 156 is connected to the display 158a of the operation panel apparatus 158.

In the main body controller 150, the CPU 151 performs arithmetic processing according to a procedure described in the imaging program 153a and the instruction received through the touch detector 158b, thereby functioning as a physique setting unit (subject physique setting unit) 151a that can set the size of the physique of the head P and a turning controller 151b that controls the turning mechanism 132 and the turning axis moving mechanism 134 in performing the X-ray imaging such as the X-ray CT imaging. The physique setting unit 151a can be called a head size setting unit. The CPU 151 controls the turning mechanism 132 and the turning axis moving mechanism 134 to turn the X-ray generator 126 and the X-ray detector 128 around the head P, and can obtain detection results of the X-rays detected by the X-ray detectors 128, 128b through the head P. The CPU 151 also functions as an imaging region setting unit 151c that sets the imaging region. For example, the setting of the spatial position of the imaging region or the setting of expansion of the imaging region can be performed as the setting of the imaging region.

The imaging program 153a and the reference table 153b are previously stored in the storage 153. Alternatively, the imaging program 153a and the reference table 153b can be provided to the existing X-ray CT imaging apparatus or the information processing main body that controls the X-ray CT imaging apparatus in the form of being recorded on a recording medium such as a CD-ROM, a DVD-ROM, or an external flash memory, or by download from an external server through a network. Because the CPU 151 and the RAM 152 include circuits, and many of the other elements also include circuits or configurations connected by circuits, the body controller 150 is an element that is mechanically constructed with circuits. The turning controller 151b is a circuit that mechanically processes the turning control according to the program. Similarly, the physique setting unit 151a is a circuit that performs processing of setting the physique of the subject from physique data of the subject according to the program, and the imaging region setting unit 151c is a circuit that performs processing of setting the imaging region.

The X-ray image processing apparatus 180 generates X-ray image data 185b based on the imaging data from the imaging main body 120. The information processing main body 182 is constructed with a computer in which a CPU 183 that is at least one processor, a RAM 184, a storage 185, an input and output unit 186, an operation input unit 189a, and an image output unit 188a are mutually connected through a bus line 182a. The storage 185 is constructed with a flash memory or a nonvolatile storage device such as a hard disk drive, and an image processing program 185a with which the information processing main body 182 generates the X-ray image data 185b based on the imaging data from the imaging main body 120 and X-ray image data 185b are stored in the storage 185. Management data in which the X-ray image data 185b is correlated with specific information about the head P (specific information about a patient) can be stored in the storage 185. The X-ray image processing apparatus 180 receives data relating to an imaging condition from the main body controller 150, and can store the data relating to an imaging condition in the storage 185 while correlating the data relating to an imaging condition with the generated X-ray image data 185b. The RAM 184 serves as a work area when the CPU 183 performs predetermined processing. The input and output unit 186 is connected to the imaging main body 120, and the X-ray imaging data obtained by the imaging main body 120 is input to the input and output unit 186 through the input and output unit 186. The operation input unit 189a is connected to the operation unit 189, and the image output unit 188b is connected to the display 188.

In the information processing main body 182, the CPU 183 performs the arithmetic processing according to the image processing program 185a, thereby performing the processing as the image processor that generates the desired X-ray image data based on the X-ray imaging data obtained by the imaging main body 120. That is, data such as the CT image, the panoramic image, and the cephalogram image is generated in response to an instruction received through the main body controller 150. The storage 185 stores the generated X-ray image data 185b.

A part or whole of the function implemented in each of the above units can be implemented in a hardware manner using a dedicated logic circuit or the like. A part or whole of the function implemented in each of the above units can be processed by a single processor in an integrated manner, or appropriately processed by a plurality of processors in a distributed manner.

<Setting of physique and turning processing during imaging>

With reference to a flowchart in FIG. 6, the imaging program 153a will be described centered on the setting of the physique and the turning processing during the imaging.

When the performance of the CT imaging is set, an operation to input the physique is received in step S11.

Figure 7:
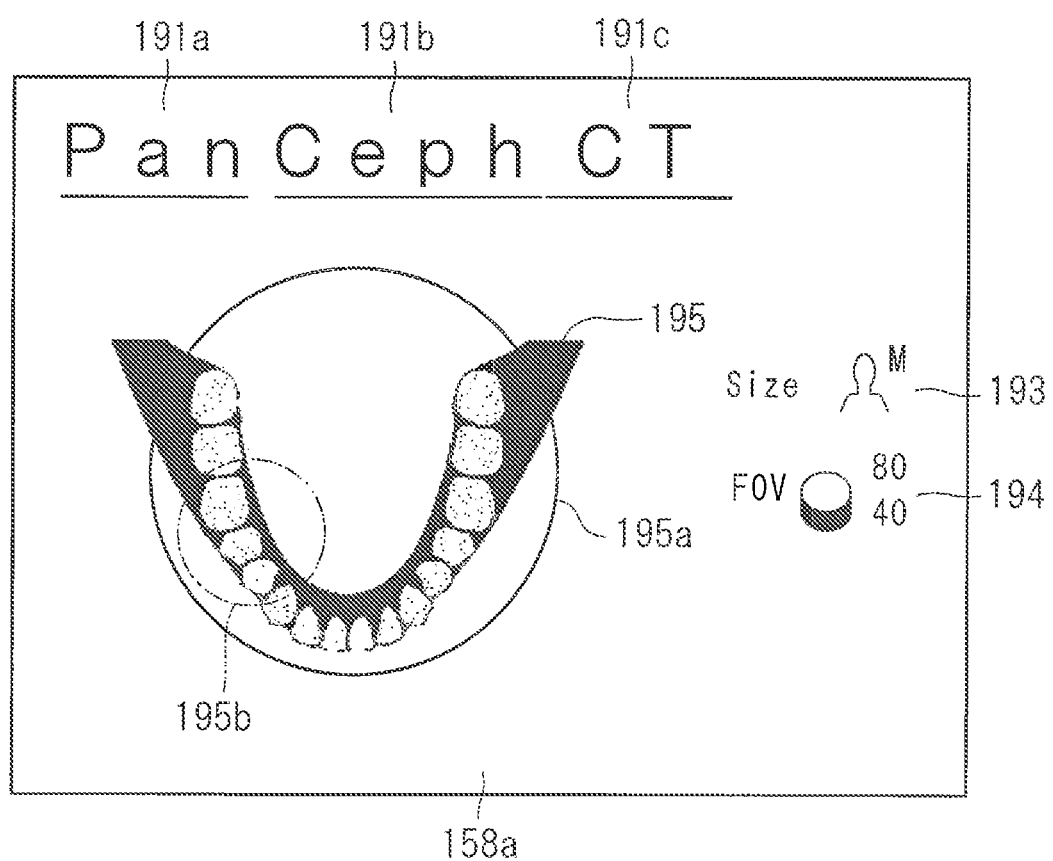
FIG. 7 is a view illustrating a display example in an operation panel apparatus.

An example of the reception of the operation to input the physique will be described. FIG. 7 is a view illustrating a display example in the operation panel apparatus 158. A panorama selection image 191a (see characters "Pan"), a cephalogram selection image 191b (see characters "Ceph"), and a CT selection image 191c (see characters "CT") are displayed on the display 158a of the operation panel apparatus 158 as the image used to select the imaging mode. A physique setting image 193 and an imaging region setting image 194 are displayed on the display 158a as the image used to set the imaging condition. In this case, the physique setting image 193 and the imaging region setting image 194 are displayed on the right side of the display 158a. An illustration image 195 is displayed on the display 158a. The illustration image 195 is displayed on the lower sides of the panorama selection image 191a, the cephalogram selection image 191b, and the CT selection image 191c in the display 158a. The illustration image 195 is an image representing the imaging region, and a dental arch is displayed as the illustration image.

The touch detector 158b is provided on the display 158a as a two-dimensional position detector that detects the touch position with respect to the display region.

When the operator touches any one of the panorama selection image 191a, the cephalogram selection image 191b, and the CT selection image 191c, the touch operation is detected by the touch detector 158b. Consequently, the main body controller 150 receives whether to perform the panoramic imaging, the cephalogram imaging, or the X-ray CT imaging.

Figure 8:
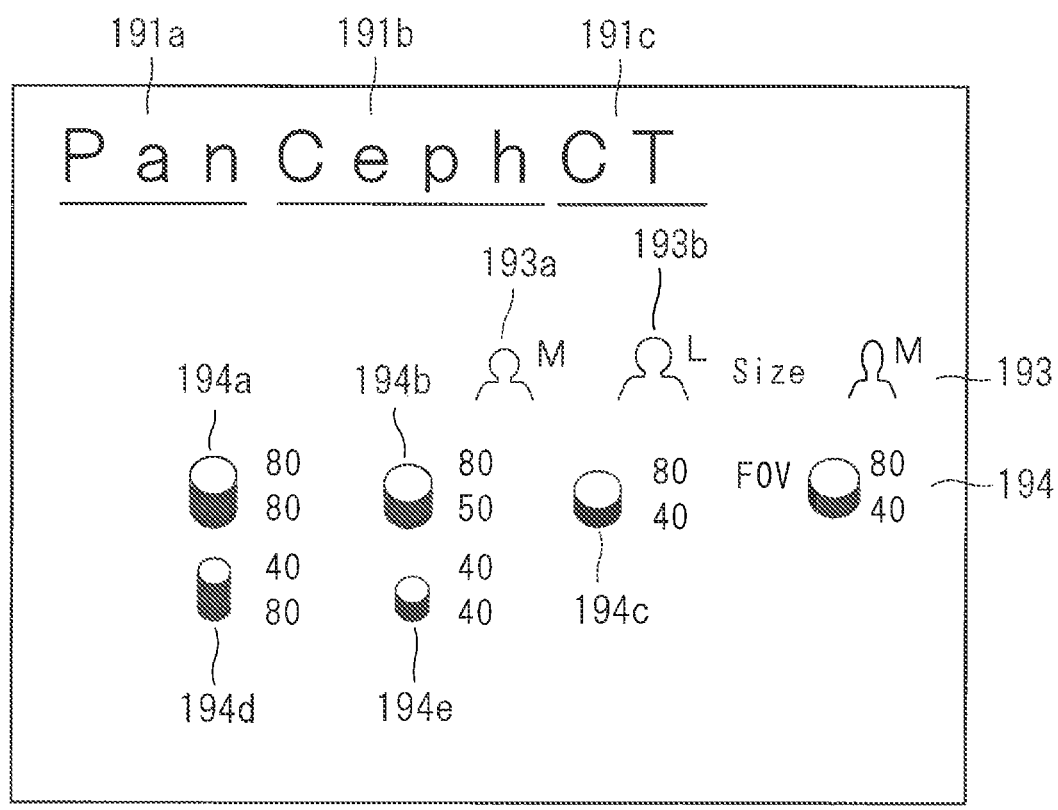
FIG. 8 is a view illustrating a display example in the operation panel apparatus.

As illustrated in FIG. 8, when the operator touches one of the physique setting image 193 and the imaging region setting image 194, a selection image corresponding to the physique setting image 193 or the imaging region setting image 194 is displayed according to the touch operation. In the example of FIG. 8, for convenience, the selection images corresponding to all the physique setting image 193 and the imaging region setting image 194 are displayed. However, actually the selection image corresponding to the touched one of the physique setting image 193 and the imaging region setting image 194 is displayed.

When the operator touches the physique setting image 193, a normal-size selection image 193a (M size) and a large-size selection image 193b (L size) are displayed as a plurality of physique selection images. The operation to input the physique of the head P is received when the user selectively touches the normal-size selection image 193a or the large-size selection image 193b.

A plurality of imaging region selection images 194a, 194b, 194c, 194d, and 194e are displayed when the operator touches the imaging region setting image 194.

The plurality of imaging region selection images 194a, 194b, 194c, 194d, 194e indicate regions in which sizes (a diameter and a height) are different from one another. The operation to set the imaging region is received when the user selectively touches any one of the plurality of imaging region selection images 194*a*, 194*b*, 194*c*, 194*d*, 194*e*.

With reference to FIG. 7, the imaging region 195*a* (or the imaging region 195*b*) is displayed while superimposed on the illustration image 195. A circle having a size corresponding to the imaging region set through the imaging region setting image 194 is displayed as the imaging regions 195*a*, 195*b*. The imaging region 195*a* is an image that is displayed when the imaging region where the whole of the dental arch is set to the target is selected, and the imaging region 195*b* is an image that is displayed when the imaging region where a part of the dental arch is set to the target is selected. In particular, when the imaging region 195*b* is selected, the operator touches any position of the illustration image 195 to move the imaging region 195*b* to a position where a part of the dental arch is designated. Consequently, the imaging region can be designated at any position of the dental arch (for example, a front tooth region, a right molar region, a left molar region). In the drawing, in order to clearly illustrate a difference, the difference between the imaging regions 195*a*, 195*b* is illustrated with some emphasis. At this point, the description will be made on the assumption that the X-ray CT imaging is performed with the whole dental arch that is the jaw region of the head P as the X-ray CT imaging region R.

In the above example, the designation of the imaging mode, the setting of the physique, the designation of the imaging region, and the like are performed using the touch panel. Alternatively, various settings can be received through a switch (push button) that physically receives the operation.

Figure 6:
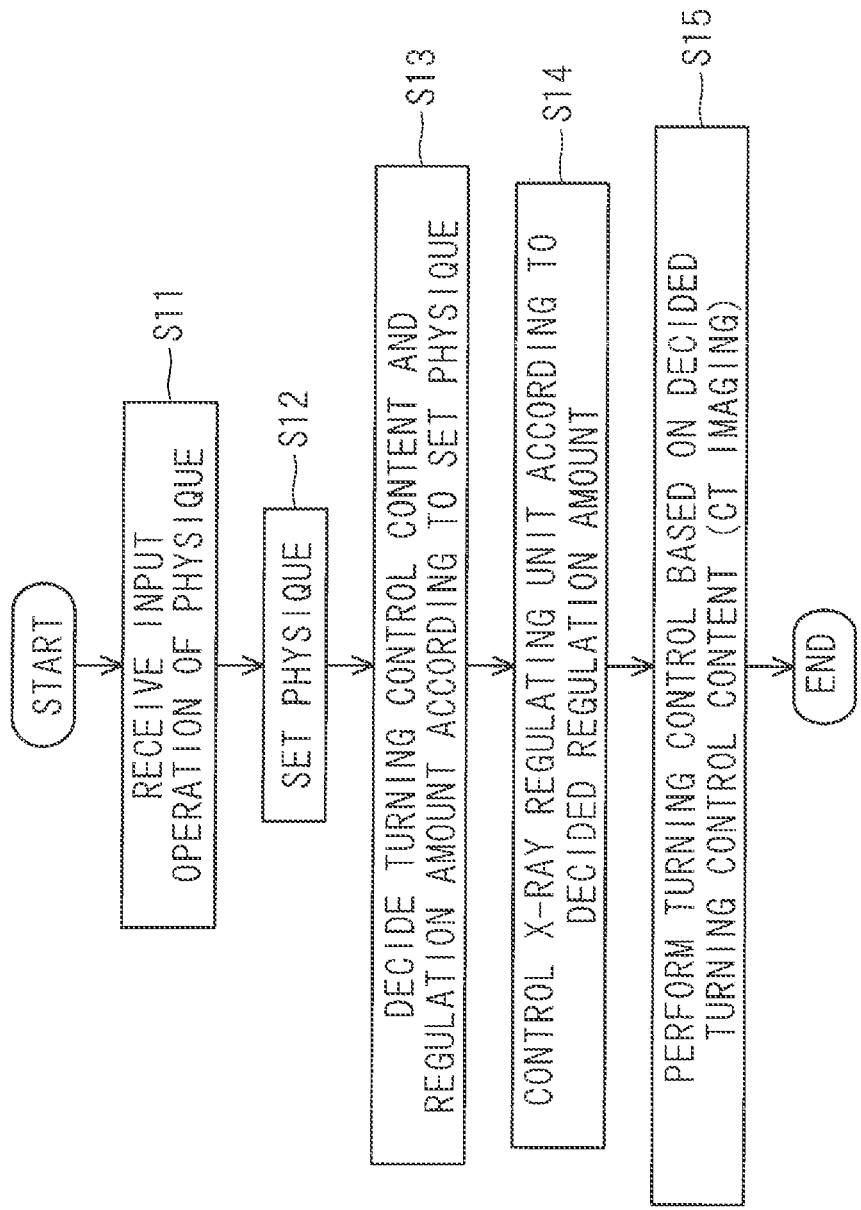
FIG. 6 is a flowchart illustrating a processing example of an imaging program.

With reference to FIG. 6, in step S12, when the physique setting unit 151*a* receives the operation to input the physique of the head P through the operation panel apparatus 158, the setting of the physique of the head P is performed according to the received content. The physique setting unit 151*a* receives the input operation to select one of the normal-size selection image 193*a* and the large-size selection image 193*b*, which are physique sizes of a plurality of selection candidates, through the operation panel apparatus 158, thereby setting the physique of the head P.

In step S13, the turning control content and the regulation amount are determined according to the set physique. The turning control content indicates how to turn the X-ray generator 126 and the X-ray detector 128 around the head P with what kind of trajectory. The turning control content is expressed by the trajectory of at least one of the X-ray generator 126 and the X-ray detector 128, the fixed position or movement trajectory of the mechanical turning axis X1 during the turning, or the position coordinates or movement coordinates of the X-direction drive unit 136 and the Y-direction drive unit 138 with respect to a turning speed of the turning mechanism 132.

When the turning control content is decided, the separation distance D is decided on the assumption that the separation distance is the distance that is smaller one of the distance between the center A of the imaging region R and the X-ray generator 126 and the distance between the center A of the imaging region R and the X-ray detector 128 in turning the X-ray generator 126 and the X-ray detector 128 around the center A of the imaging region R. In this case, because the turning axis X1 is located closer to the X-ray detector 128 in the turning support 124, the separation distance D is the distance between the center A of the imaging region R and the X-ray detector 128. The position of the imaging region R in the X-ray CT imaging apparatus 110 is known because the head P is held at a fixed position by the head fixing apparatus 142 and the imaging region is set as described above.

Because the distance of the X-ray generator 126 to the center A of the imaging region R is also decided, magnification is also decided when the X-ray emitted from the X-ray generator 126 is incident on the X-ray detector 128 through the head P. Assuming that DA is the distance between the X-ray generator 126 and the X-ray detector 128, and that D1 is the distance between the X-ray generator 126 and the center A of the imaging region R, magnification m becomes m=DA/D1.

Because a minimum width of the X-ray is decided in order to transmit the X-ray generated from the X-ray generator 126 through the whole imaging region R when the turning control content is decided, an X-ray regulating width (X-ray regulating hole) that should be regulated by the X-ray detector 128 can also be set in a range larger than the minimum width and in a range that prevents surroundings of the range larger than the minimum width from being excessively irradiated with the X-ray.

For example, the decision of the turning control content and the regulation amount according to the set size of physique can be performed by referring to the reference table in FIG. 9. That is, the reference table in which the turning control content, the separation distance D (magnification m), and the regulating width W are correlated with the physique of the head P is previously registered. In the example of FIG. 9, for the normal physical shape P(M), the mechanical turning axis X1 is turned while matched with the center A of the imaging region R, the separation distance D(M) (magnification m(M)), and the regulating width W(M) are correlated with one another as the turning control content. For the physique P(L) larger than the normal physique P(M), the mechanical turning axis X1 is turned with a radius r about the center A of the imaging region R, the separation distance D(L) (magnification factor m(L)), and a regulating width W(L) are correlated with one another as the turning control content. The separation distance D(M), the magnification m(M), the regulating width W(M), the separation distance D(L), the magnification m(L), the regulating width W(L), and the radius r are defined by a specific numerical value, and the physique P(L) is larger than the physique P(M), separation distance D(M)<separation distance D(L), magnification m(M)<magnification m(L), and regulating width W(M)<regulating width W(L) hold.

In step S14, the X-ray regulating unit 129 is controlled according to the regulating widths W(M), W(L) that are the decided regulation amount such that the X-ray having the width corresponding to the imaging region R is emitted from the X-ray generator 126.

In step S15, the CT imaging is performed by performing the turning control based on the decided turning control content. That is, when the X-ray CT imaging is performed by irradiating the head P with the X-ray generated from the X-ray generator 126, the position control of the turning axis X1 is performed according to the size of the physique of the head P that is the subject set by the physique setting unit 151*a*.

An example in which the drive control causing the turning mechanism 32 to perform the above combined motion and the drive control turning the turning support 124 in the state in which the mechanical turning axis X1 is fixed to the position of the center A of the imaging region R are switched according to the size of the physique of the head P which is the subject set by the physique setting unit 151*a* will be described below.

In this case, when the X-ray generator 126 and the X-ray detector 128 are turned around the center A of the imaging region R, the position of the mechanical turning axis X1 with respect to the center A of the imaging region R can be controlled according to the physique P(M) or the physique P(L) of the head P set by the physique setting unit 151*a* such that the separation distance D (L) when the set physique is the first physique P(L) is larger than the separation distance D(M) when the set physique is the second physique P(M) small than the first physique P(L).

An example in which, according to the physique of the head P set by the physique setting unit 151*a*, the drive control causing the turning support 124 to perform the combined motion is performed when the set physique of the head P is the first physique P(L), and the drive control turning the turning support 124 in the state in which the mechanical turning axis X1 is fixed to the center position of imaging region R when the set physique of the head P is the second physique P(M) smaller than the first physique P(L) will be described below.

Switching of the drive control with respect to the size of the physique can be reversed depending on the position of the turning axis X1 with respect to the X-ray generator 126 and the X-ray detector 128. For example, when the turning axis X1 is located at a position close to a middle between the X-ray generator 126 and the X-ray detector 128, the drive control turning the turning support 124 can be performed on the first physique P(L) having the set relatively large physique of the head P while the mechanical turning axis X1 is fixed to the center position of the imaging region R, and the physique of the set head P is relatively small the drive control causing the turning support 124 to perform the combined motion can be performed on the second physique P(M) having the set relatively small physique of the head P.

Figure 10:
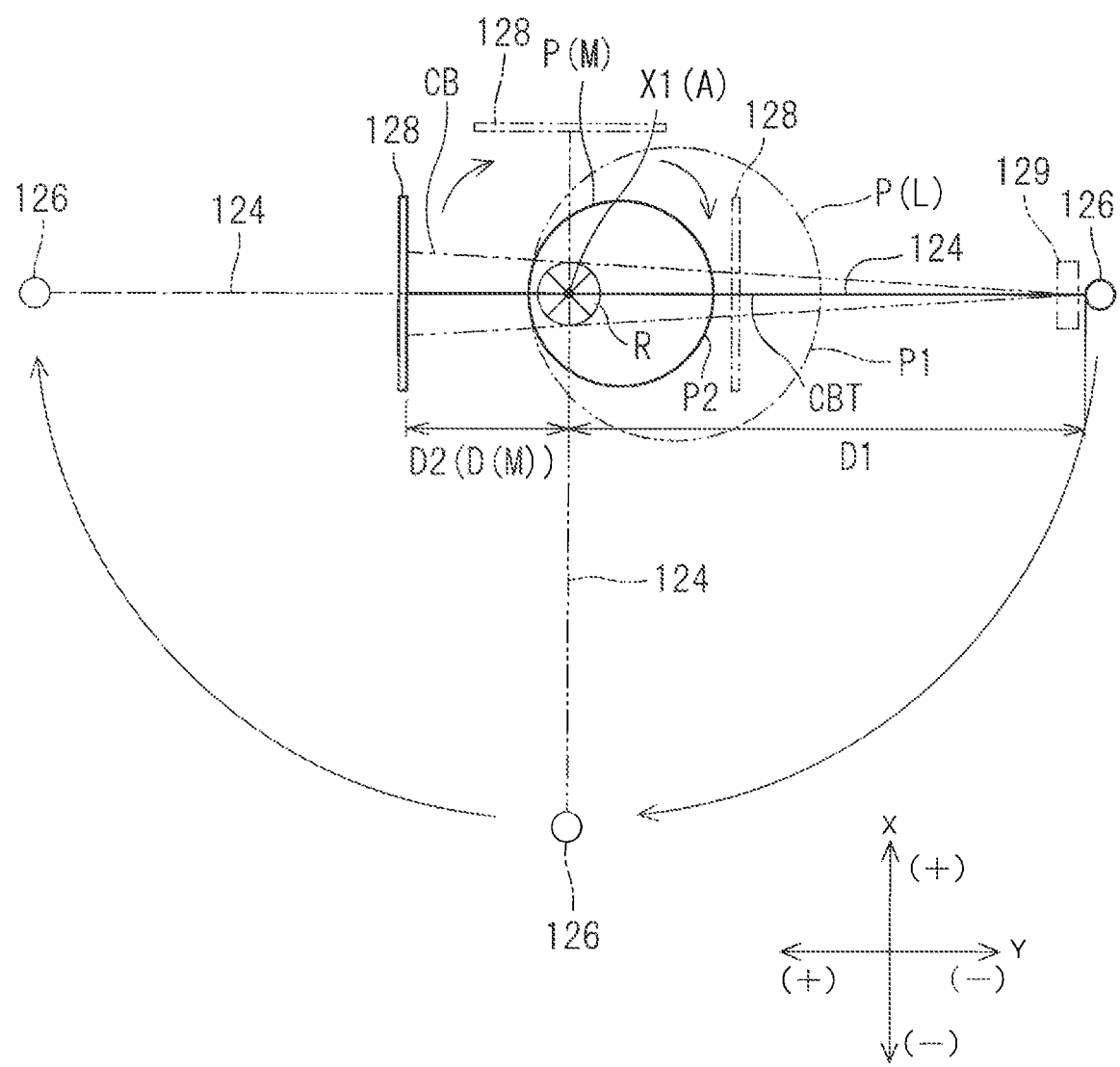
FIG. 10 is a view illustrating a turning action example when a physique is relatively small.
Figure 11:
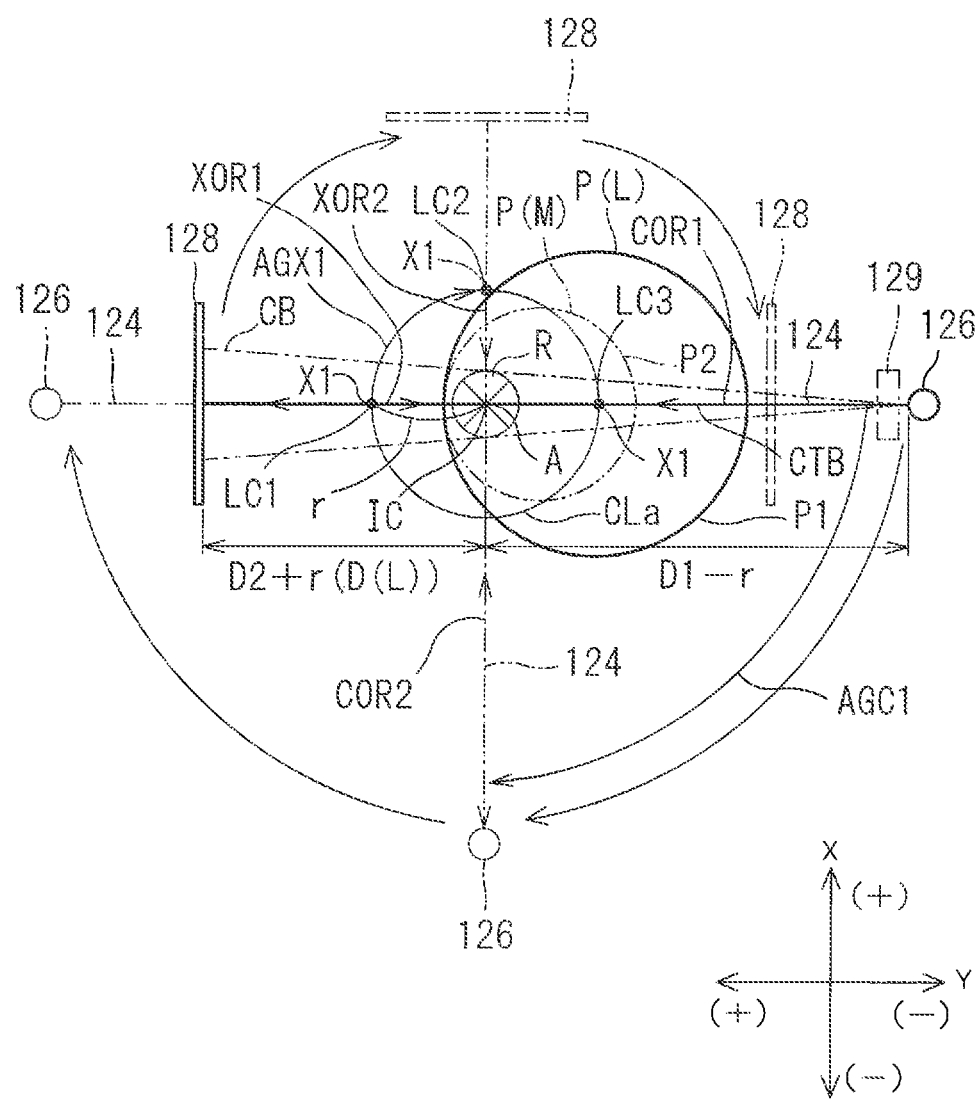
FIG. 11 is a view illustrating a turning action example in the case where the physique is relatively large.

An example of the turning action will be described in more detail with reference to FIGS. 10 and 11. FIG. 10 is an explanatory view illustrating turning action when the physique is the relatively small second physique P(M), and FIG. 11 is an explanatory view illustrating turning action when the physique is the relatively large first physique P(L). FIGS. 10 and 11 are principle explanatory views when the turning action is viewed from the Z-axis direction. Although FIGS. 10 and 11 illustrate the state in which the turning support 124 is turned 180 degrees, the CT imaging can be performed by turning the turning support 124 by 360 degrees according to the setting.

In the example of FIGS. 10 and 11, the position of the mechanical turning axis X1 is located closer to the X-ray detector 128 than the intermediate point between the X-ray generator 126 and the X-ray detector 128 on the turning support 124.

For the relatively small second physique P(M), as illustrated in FIG. 10, the turning support 124 is turned while the mechanical turning axis X1 is matched with the center A of the imaging region R. In this case, the X-ray generator 126 and the X-ray detector 128 turn about the mechanical turning axis X1 matched with the center A of the imaging region R. The X-ray regulating unit 129 forms the X-ray into an X-ray cone beam CB. The turning support 124 is driven by the turning drive mechanism 130, the X-ray detector 128 is located close to the +Y-direction in FIGS. 10 and 11, and both ends of the spread in the x-direction of the X-ray cone beam CB contact with both ends of the spread in the x-direction of the imaging region R when viewed from a focal point of an X-ray tube of the X-ray generator 126 at the position where the X-ray generator 126 is located close to the −Y-direction, a center beam CTB that equally divided a spread angle in the x-direction of the X-ray cone beam CB has a positional relationship in which the center beam CTB passes through the center A of the imaging region R, and the positional relationship is maintained during the imaging and the turning of the turning support 124. During the turning, the distance between the center A of the imaging region R and the X-ray generator 126 is maintained at D1, and the distance between the center A of the imaging region R and the X-ray detector 128 is maintained at D2. Because the X-ray detector 128 is located closer to the center of the imaging region R than the X-ray generator 126 on the orbits of the X-ray generator 126 and the X-ray detector 128, which are set for the imaging region R, during the X-ray imaging, the separation distance D(M) becomes the distance D2 between the center A of the imaging region R and the X-ray detector 128. The separation distance D(M) is set larger than the maximum distance between the center A of the imaging region R and a surface of the head P(P2) having the smaller physique P(M) in the direction orthogonal to the turning axis X1. For this reason, the X-ray detector 128 can turn around the head P(P2) without contacting with the head P(P2) having the smaller physique P(M). The X-ray generator 126 turns at a position farther from the center A of the imaging region R than the X-ray detector 128, so that the X-ray generator 126 can turn around the head P(P2) without contacting with the head P(P2). The separation distance D (not illustrated) becomes the distance between the center A of the imaging region R and the X-ray generator 126 when the X-ray generator 126 is closer to the imaging center A than the X-ray detector 128 on the orbits of the X-ray generator 126 and the X-ray detector 128, which set for the imaging region R, during the X-ray imaging.

Because the chin rest 142*a* is commonly used for the head P1 and the head P2, the imaging region R becomes the same position in the front of the head in the head P1 and the head P2, and an occipital region of the head P1 occupies a larger region than an occipital region of the head P2 on the −Y-side. For the relatively large first physique P(L) (head P1), when the X-ray detector 128 turns in the same manner as described above, there is a possibility that the X-ray detector 128 abuts on the head P(P1) having the first physique P(L).

For this reason, for the relatively large first physique P(L), as illustrated in FIG. 11, the turning support 124 is turned about the mechanical turning axis X1 while the mechanical turning axis X1 is turned with the radius r about the center A of the imaging region R. That is, the mechanical turning axis X1 moves on a circular orbit CLa having the radius r. That is, the position of the mechanical turning axis X1 with respect to the center A of the imaging region R is controlled such that the mechanical turning axis X1 is moved away from the center A of the imaging region R. More specifically, the mechanical turning axis X1 is turned with the radius r about the center A of the imaging region R by the turning axis moving mechanism 134 in synchronization with the turning of the turning support 124 about the mechanical turning axis X1 using the turning mechanism 132. In order to move the X-ray detector 128 away from the center A of the imaging region R, the mechanical turning axis X1 is moved away from the center A of the imaging region R toward the side of the X-ray detector 128. That is, the mechanical turning axis X1 turns around the center A of the imaging region R while maintaining the positional relationship provided between the center A of the imaging region R and the X-ray detector 128.

The mechanical turning axis X1 is located at a position LC1 shifted onto the +Y-side from the center A of the imaging region R in timing when the X-ray generator 126 is located on the −Y-side while the X-ray detector 128 is located on the +Y-side, the mechanical turning axis X1 is located at a position LC2 shifted onto the +X-side from the center A of the imaging region R in timing when the X-ray generator 126 is located on the −X-side while the X-ray detector 128 is located on the +X-side, and the mechanical turning axis X1 is located at a position LC3 shifted onto the −Y-side from the center A of the imaging region R in timing when the X-ray generator 126 is located on the +Y-side while the X-ray detector 128 is located on the −Y-side.

Although not illustrated, assuming that the X-ray generator 126 is located on the +X-side while the X-ray detector 128 is located on the −X-side, the mechanical turning axis X1 is shifted onto the −X-side from the center A of the imaging region R.

The synchronization between the turning of the turning support 124 about the mechanical turning axis X1 and the turning of the mechanical turning axis X1 about the center A of the imaging region R will further be described with reference to FIG. 11. The mechanical turning axis X1 is located at the position LC1 deviating from the center A, and the whole imaging region R is irradiated from the −Y-direction toward the +Y-direction with the X-ray cone beam CB in the illustrated example. It is assumed that an orientation COR1 is an orientation in which the center beam CTB travels toward the imaging region R, namely, the orientation toward the center A in the illustrated example, and that an orientation XOR1 is an orientation from the mechanical turning axis X1 toward the center A. In the illustrated example, the whole imaging region R is irradiated from the −X-direction to the +X-direction with the X-ray cone beam CB at a point of time the mechanical turning axis X1 turns about the center A to the position LC2 deviating from the center A along the circular orbit CLa having the radius r while the turning support 124 turns about the mechanical turning axis X1. It is assumed that an orientation COR2 is the orientation in which the center beam CTB travels toward the imaging region R, namely, the orientation toward the center A in the illustrated example, and that an orientation XOR2 is the orientation from the mechanical turning axis X1 toward the center A. It is assumed that AGC1 is a displacement angle amount from the orientation COR1 to the orientation COR2, and that AGX1 is a displacement angle amount from the orientation XOR1 to the orientation XOR2. The displacement from the orientation COR1 to the orientation COR2 and the displacement from the orientation XOR1 to the orientation XOR2 are identical to each other as a turning direction in which the center A is set to the turning center, and the displacement angle amount AGC1 and the displacement angle amount AGX1 are equal to each other. The turning movement of the turning support 124 is performed by the turning drive mechanism 130. In the illustrated example, the turning of the turning support 124 is performed by the turning mechanism 132, and the movement of the mechanical turning axis X1 is performed by the turning axis moving mechanism 134. The above synchronization is performed while this relationship is kept.

At this point, the coordinate of the mechanical turning axis X1 is temporarily considered while leaving FIG. 11. For example, assuming that (X(a),Y(a)) is the coordinates of X and Y in the XYZ-coordinate system of the center A of the imaging region R, and that θ (an angle rotating counterclockwise from the direction in which the X-ray generator 126 is located on the +X-side while the X-ray detector 128 is located on the −X-side) is the turning angle of the turning support 124 by the turning mechanism 132, the turning mechanism 132 and the turning axis moving mechanism 134 are controlled such that an X-coordinate of the mechanical turning axis X1 becomes "X(a)-rcosθ" by the X-direction drive unit 136, and such that a Y-coordinate of the mechanical turning axis X1 becomes "Y(a)-rsinθ" by the Y-direction drive unit 138. The control content can similarly be applied to the following modifications in which the mechanical turning axis X1 is turned.

In this case, the X-ray generator 126 and the X-ray detector 128 turn about the mechanical turning axis X1. With reference to FIG. 11, based on the distance D1 between the center A of the imaging region R and the X-ray generator 126 in the case of FIG. 10 (in the case of FIG. 10, the distance D1 is the same as the distance between the mechanical turning axis X1 and the X-ray generator 126), the distance between the center A of the imaging region R and the X-ray generator 126 during the turning is distance D1−radius r, and is kept constant. Based on the distance D2 in the case of FIG. 10 (in the case of FIG. 10, the distance D2 is the same as the distance between the mechanical turning axis X1 and the X-ray detector 128), the distance between the center A of the imaging region R and the X-ray detector 128 during the turning is distance D2+radius r, and is kept constant. The smaller one becomes the separation distance D(L). At this point, it is assumed that the radius r is decided within the range of (distance D1−radius r)≥ (distance D2+radius r). For this reason, the separation distance D(L) is distance D2+radius r. The separation distance D(L) is set larger than the maximum distance between the center A of the imaging region R and the surface of the head P(P1) having the larger physique P(L) in the direction orthogonal to the turning axis X1. Consequently, the X-ray detector 128 can turn around the head P(P1) having the larger physique P(L) without contacting with the head P(P1). The X-ray generator 126 turns at a position as far as or far away from the X-ray detector 128 with respect to the center A of the imaging region R, so that the X-ray generator 126 can turn around the head P(P1) without contacting with the head P(P1). The maximum distance to the surface of the head P(P1) can be set to the maximum distance in the range where the X-ray generator 126 or the X-ray detector 128 relating to the smaller separation distance D(L) turns. For example, for the turning angle of the turning support 124 less than 360° such as the turning angle of 180°, the maximum distance in the range of the movement orbit of the X-ray generator 126 or the X-ray detector 128 relating to the smaller separation distance D(L) can be targeted except for the occipital region when the X-ray generator 126 or the X-ray detector 128 relating to the smaller separation distance D(L) does not turn to the occipital region.

In the embodiment of FIG. 11, during the X-ray CT imaging, a bias of the mechanical turning axis X1 with respect to the center A is generated on the side of the X-ray detector 128. The direction from the center A toward the mechanical turning axis X1 and the direction from the X-ray generator 126 toward the X-ray detector 128 are maintained in parallel.

Hereinafter, the turning center of the X-ray generator 126 and the X-ray detector 128 is referred to as an imaging turning center IC.

When the mechanical turning axis X1 is subjected to the control in FIG. 11, the X-ray generator 126 and the X-ray detector 128 turn with the center A of the imaging region R as the imaging turning center IC. As described above, the imaging turning center IC can be generated when the mechanical turning axis X1 is subjected to two-dimensional movement control.

When the relatively small second physique P(M) in FIG. 10 is compared to the relatively large first physique P(L) in FIG. 11, the relatively small second physique P(M) is smaller than the relatively large first physique P(L) in the distance between the center A of the imaging region R and the X-ray generator 126. For this reason, in order to transmit the X-rays emitted from the X-ray generator 126 through the whole imaging region R, the regulating width W(M) of the X-ray by the X-ray regulating unit 129 for the second physique P (M) can be set smaller (the passage allowable width is widened) than the regulating width W(L) of the X-ray by the X-ray regulating unit 129 for the first physique P(L). Consequently, the X-ray can be emitted in the range corresponding to the imaging region R. That is, the regulating widths W(L), W(M) are set according to the distance between the center A of the imaging region R and the X-ray generator 126 when the X-ray generator 126 and the X-ray detector 128 are turned around the center A of the imaging region R, and the X-ray regulating unit 129 adjusts the regulation amount of the X-ray generated from the X-ray generator 126 according to the distance between the center A of the imaging region R and the X-ray generator 126. The regulation amount of the main X-ray can similarly be adjusted in each modification.

In the regulating width W of the X-ray by the X-ray regulating unit 129, only a regulating width Wx in the x-direction can be adjusted, and a regulating width Wz in the z-direction (vertical direction) can also be adjusted.

By turning the X-ray generator 126 and the X-ray detector 128 around the imaging region R of the head P, the X-ray image data necessary for the generation of the X-ray CT image of the imaging region R is obtained, and the X-ray CT image is generated based on the obtained data.

<Effect>

In the X-ray CT imaging apparatus 110 configured as described above, the position control of the turning axis X1 is performed according to the size of the physique of the head P that is the subject set by the physique setting unit 151a, so that the X-ray generator 126 and the X-ray detector 128 turning around the head P can be prevented from contacting with the head P.

In this case, when the X-ray generator 126 and the X-ray detector 128 are turned around the center A of the imaging region R, assuming that the separation distance is the smaller one of the distance between the center A of the imaging region R and the X-ray generator 126 and the distance between the center A of X and the X-ray detector 128, the position control of the mechanical turning axis X1 with respect to the center A of the imaging region R is performed according to the physiques P(L), P(M) of the head P set by the physique setting unit 151a such that the separation distance for the large physique P (L) of the head P is larger than the separation distance for the small physique P (M) of the head P, so that the X-ray generator 126 and the X-ray detector 128 turning around the head P can be prevented from contacting with the head P.

The turning trajectory of the X-ray detector 128 is changed according to the size of the physiques P(L), P (M) of the head P, so that the X-ray CT imaging can be performed by bringing the X-ray detector 128 as close as possible to the head P while the contact between the X-ray detector 128 and the head P is suppressed. Consequently, the clear X-ray image can be generated.

The turning axis moving mechanism 134 is provided on not the side of the turning support 124, but the side of the horizontal arm 123 with respect to the turning mechanism 132. Consequently, a weight of the turning support 124 can be reduced, and a load turning the turning support 124 can be reduced as much as possible.

When the X-ray CT imaging is performed by irradiating the head P with the X-ray generated from the X-ray generator 126, for the head P1 of a relatively large first physique P (L), the turning axis moving mechanism 134 rotates the mechanical turning axis X1 about the center A of the imaging region R in synchronization with the turning of the turning support 124 about the mechanical turning axis X1 using the mechanism 132, whereby the separation distance can be adjusted while the X-ray generator 126 and the X-ray detector 128 are turned along the orbit as close as possible to the circle. The magnification ratio can be kept constant as much as possible by turning the X-ray generator 126 and the X-ray detector 128 along the orbit as close as possible to the circle.

For the head P2 of the relatively small second physique P(M), the X-ray generator 126 and the X-ray detector 128 are turned around the turning axis X1 while the turning center of the mechanical turning axis X1 is fixed to the position of the center A of the imaging region R, so that accuracy of the turning of the imaging system constructed with the X-ray generator 126 and the X-ray detector 128 can be enhanced to obtain the clearer X-ray CT image.

In the example of FIGS. 10 and 11, the mechanical turning axis X1 is located closer to the X-ray detector 128 than the intermediate point between the X-ray generator 126 and the X-ray detector 128 on the turning support 124. For this reason, for the head P2 of the relatively small second physique P(M), the magnification ratio of the image can be reduced when the X-ray generator 126 and the X-ray detector 128 are turned around the turning axis X1 while the turning center of the mechanical turning axis X1 is fixed to the position of the center A of the imaging region R. Typically, a focal point of an X-ray tube of the X-ray generator 126 is not a perfect point light source, but has a small constant area, so that a degree of contour blurring can be decreased by reducing the magnification ratio.

When the X-ray generator 126 and the X-ray detector 128 are turned as described above, the X-ray regulating unit 129 adjusts the regulation amount of the X-ray generated from the X-ray generator 126 according to the distance of the X-ray generator 126 to the center A of the imaging region R, which allows the X-ray having a proper width to be incident on the imaging region R of the head P according to the separation distance.

The mechanical turning axis X1 is along the vertical direction, so that the X-ray generator 126 and the X-ray detector 128 can be turned around the axis along the vertical direction. Consequently, the X-ray CT imaging is suitably performed with the head P of a standing or sitting human body as the subject.

The X-ray CT imaging is performed with the jaw region of the head P that is the subject as the imaging region R, so that the X-ray generator 126 and X-ray detector 128 can be prevented from contacting with the head P according to the physique of the head P when the CT imaging is performed on the jaw region.

The distance of the X-ray generator 126 to the center A of the imaging region R and the distance of the X-ray detector 128 to the center A of the imaging region R are kept constant while the CT imaging is performed, so that the X-ray CT imaging can be performed while the magnification ratio is kept constant.

For the head P having the relatively small second physique P(M), the mechanical turning axis X1 is matched with the center A of the imaging region R, so that the CT imaging can be performed while a driving load on the apparatus is reduced. On the other hand, for the head P having the relatively large first physique P(L), the position of the mechanical turning axis X1 with respect to the center A of the imaging region R is controlled such that the position of the mechanical turning axis X1 is moved away from the center A of the imaging region R, so that the separation distance can be increased to prevent the contact of the X-ray generator 126 and the X-ray detector 128 with the head P.

In the X-ray CT imaging apparatus 110, the operator or the like of the X-ray CT imaging apparatus 110 performs the input operation through the operation panel apparatus 158, which allows the setting of the physique of the head P.

In particular, the operator or the like can easily perform the input operation by selecting one of the normal-size selection image 193a and the large-size selection image 193b that are the physiques of the plurality of selection candidates through the operation panel apparatus 158.

However, the size of the physique can be input when the operator or the like inputs the size of the physique using a ten key or the like.

MODIFICATIONS

Various modifications will be described below based on the first embodiment or the second embodiment.

First Modification

In the second embodiment, by way of example, the drive control that causes the turning support 124 to perform the combined motion and the drive control that causes the turning support 124 to turn while fixing the mechanical turning axis X1 to the position of the center A of the imaging region R are switched according to the size of the physique of the head P that is the subject set by the physique setting unit 151a.

An example, in which the distance of the mechanical turning axis X1 with respect to the center A of the imaging region R according to the size of the physique of the head P that is the subject set by the physique setting unit 151a when the turning support 124 performs the combined motion, will be described in a first modification of FIGS. 12 and 13. That is, an example, in which the position control of the mechanical turning axis X1 with respect to the center A of the imaging region R is performed such that the position of the mechanical turning axis X1 is moved away from the center A of the imaging region R in both the relatively small second physique P(M) and the relatively large first physique P(L), will be described in the first modification.

Figure 13:
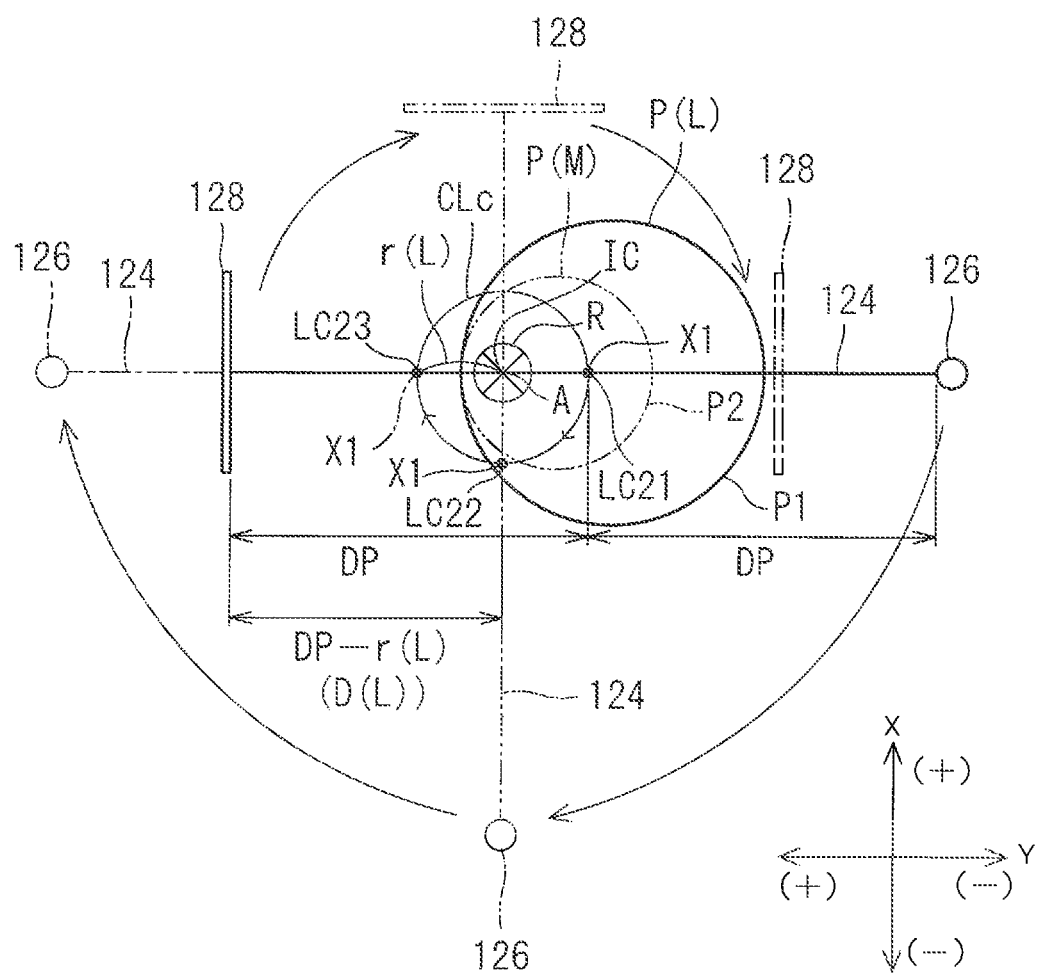
FIG. 13 is a view illustrating a turning action example when the physique is relatively large in the first modification.

FIG. 12 is an explanatory view illustrating the turning action for the relatively small second physique P(M), and FIG. 13 is an explanatory view illustrating the turning action for the relatively large first physique P(L). In the first modification, the mechanical turning axis X1 is located at the central position between the X-ray generator 126 and the X-ray detector 128. For this reason, the distance of the X-ray generator 126 to the mechanical turning axis X1 and the distance of the X-ray detector 128 to the turning axis X1 are equal to each other. Although FIGS. 12 and 13 illustrate the state in which the turning support 124 is turned by 180 degrees, the CT imaging can be performed by turning the turning support 124 by 360 degrees according to the setting.

For the relatively small second physique P (M), as illustrated in FIG. 12, the turning support 124 is turned about the mechanical turning axis X1 while the mechanical turning axis X1 is turned with a radius r(M) about the center A of the imaging region R. More specifically, the mechanical turning axis X1 is turned with the radius r(M) about the center A of the imaging region R by the turning axis moving mechanism 134 in synchronization with the turning of the turning support 124 about the mechanical turning axis X1 using the turning mechanism 132. That is, the mechanical turning axis X1 moves on a circular orbit CLb having the radius r(M). In order to bring the X-ray detector 128 close to the center A of the imaging region R, the mechanical turning axis X1 is moved away from the center A of the imaging region R toward the side of the X-ray generator 126. That is, the mechanical turning axis X1 turns around the center A of the imaging region R while maintaining the positional relationship provided between the center A of the imaging region R and the X-ray generator 126.

The mechanical turning axis X1 is located at a position LC11 shifted onto the −Y-side from the center A of the imaging region R in timing when the X-ray generator 126 is located on the −Y-side while the X-ray detector 128 is located on the +Y-side, the mechanical turning axis X1 is located at a position LC12 shifted onto the −X-side from the center A of the imaging region R in timing when the X-ray generator 126 is located on the −X-side while the X-ray detector 128 is located on the +X-side, and the mechanical turning axis X1 is located at a position LC13 shifted onto the +Y-side from the center A of the imaging region R in timing when the X-ray generator 126 is located on the +Y-side while the X-ray detector 128 is located on the −Y-side.

Although not illustrated, assuming that the X-ray generator 126 is located on the +X-side while the X-ray detector 128 is located on the −X-side, the mechanical turning axis X1 is shifted onto the +X-side from the center A of the imaging region R.

When the CT imaging is performed by turning the X-ray generator 126 and the X-ray detector 128 while the mechanical turning axis X1 is matched with the center A of the imaging region R, a degree to which the X-ray detector 128 is moved away from the imaging region R is excessively large, so that the orbit in FIG. 12 is preferably used in the case that the X-ray detector 128 is brought as close as possible to the imaging region R while the contact with the head P2 is avoided.

In this case, assuming that DP is the distance of the X-ray generator 126 to the mechanical turning axis X1 and the distance of the X-ray detector 128 to the turning axis X1, the distance between the center A of the imaging region R and the X-ray generator 126 during the turning is distance DP+radius r(M), and is kept constant. The distance between the center A of the imaging region R and the X-ray detector 128 during the turning is distance DP−radius r(M), and is kept constant. Distance DP−radius r(M), which is the smaller one, becomes the separation distance D(M). This separation distance D(M) is set larger than the maximum distance between the center A of the imaging region R and the surface of the head P(P2) having the smaller physique P(M) in the direction orthogonal to the turning axis X1. For this reason, the X-ray detector 128 can turn around the head P(P2) without contacting with the head P(P2) having the smaller physique P(M). The X-ray generator 126 turns at a position farther from the X-ray detector 128 with respect to the center A of the imaging region R, so that the X-ray generator 126 can turn around the head P(P2) without contacting with the head P that is the subject.

For the relatively large first physique P(L), when the X-ray detector 128 turns in the same manner as described above, there is a possibility that the X-ray detector 128 abuts on the head P(P1) having the first physique P(L).

For this reason, in the example of FIG. 13, the turning support 124 is turned about the mechanical turning axis X1 while the mechanical turning axis X1 is turned with a radius r(L) about the center A of the imaging region R. More specifically, the mechanical turning axis X1 is turned with the radius r(L) about the center A of the imaging region R by the turning axis moving mechanism 134 in synchronization with the turning of the turning support 124 about the mechanical turning axis X1 using the turning mechanism 132. At this point, radius r(L)<radius r(M) holds. That is, the mechanical turning axis X1 moves on a circular orbit CLc having the radius r(L).

That is, also in the first physique P(L), the X-ray detector 128 is desired to be brought as close as possible to the imaging region R. As in the case of FIG. 12, in order to bring the X-ray detector 128 close to the center A of the imaging region R as compared with the case that the turning axis X1 is matched with the center A of the imaging region R, the mechanical turning axis X1 is moved away from the center A of the imaging region R toward the side of X-ray generator 126. In this case, the mechanical turning axis X1 turns around the center A of the imaging region R while maintaining the positional relationship provided between the center A of the imaging region R and the X-ray generator 126. However, as compared with the case of FIG. 12, the X-ray detector 128 is desired to be moved away from the center A of the imaging region R because of the large physique. For this reason, the turning axis X1 is turned with the radius r(L) smaller than the radius r(M).

The X-ray generator 126 and the X-ray detector 128 turn around the imaging turning center IC while the imaging turning center IC is placed on the position of the center A.

The mechanical turning axis X1 is located at a position LC21 shifted onto the −Y-side from the center A of the imaging region R in timing when the X-ray generator 126 is located on the −Y-side while the X-ray detector 128 is located on the +Y-side, the mechanical turning axis X1 is located at a position LC22 shifted onto the −X-side from the center A of the imaging region R in timing when the X-ray generator 126 is located on the −X-side while the X-ray detector 128 is located on the +X-side, and the mechanical turning axis X1 is located at a position LC23 shifted onto the +Y-side from the center A of the imaging region R in timing when the X-ray generator 126 is located on the +Y-side while the X-ray detector 128 is located on the −Y-side.

Although not illustrated, assuming that the X-ray generator 126 is located on the +X-side while the X-ray detector 128 is located on the −X-side, the mechanical turning axis X1 is shifted onto the +X-side from the center A of the imaging region R.

When the X-ray detector 128 is brought as close as possible to the imaging region R to perform the imaging while the contact with the head P1 is avoided, the orbit in FIG. 13 is preferably used.

In this case, the distance between the center A of the imaging region R and the X-ray generator 126 during the turning is distance DP+radius r(L), and is kept constant. The distance between the center A of the imaging region R and the X-ray detector 128 during the turning is distance DP−radius r(L), and is kept constant. Distance DP−radius r(L), which is the smaller one, becomes the separation distance D(L). Because of radius r(L)<radius r(M), the separation distance D(L) is larger than the separation distance D(M). The separation distance D(L) is set larger than the maximum distance between the center A of the imaging region R and the surface of the head P(P1) having the larger physique P(L) in the direction orthogonal to the turning axis X1. Consequently, the X-ray detector 128 can turn around the head P(P1) that is the subject having the larger physique P(L) without contacting with the head P(P1). The X-ray generator 126 turns at a position farther from the X-ray detector 128 with respect to the center A of the imaging region R, so that the X-ray generator 126 can turn around the head P(P1) without contacting with the head P(P1) that is the subject.

As described above, the mechanical turning axis X1 can be moved away from the center A of the imaging region R for any one of the relatively large physique P(L) and the relatively small physique P(M). In this case, the orbit on which the X-ray generator 126 and the X-ray detector 128 turn can be changed according to the size of the physique by changing the distance of the mechanical turning axis X1 to the center A of the imaging region R according to the size of the physique, and therefore the X-ray generator 126 and the X-ray detector 128 can be prevented from contacting with the head P.

When the turning axis X1 is located at a position biased to the X-ray generator 126 or the X-ray detector 128 (in particular, a largely biased position), the turning axis X1 is turned while located between the center A of the imaging region R and the X-ray generator 126 or the X-ray detector 128 on the side on which the turning axis X1 is biased, the turning radius of the X-ray generator 126 or the X-ray detector 128 on the side on which the turning axis X1 is biased with respect to the center A of the imaging region R can be increased by the turning radius of the turning axis X1. In this case, radius r(L)>radius r(M) can hold for the turning radius r(L) (the turning radius when the physique is large) of the X-ray generator 126 or X-ray detector 128 on the side on which the turning axis X1 is biased and the radius r(M) (the turning radius when the physique is small).

As described in the second embodiment, the turning support 124 can be turned about the mechanical turning axis X1 while the mechanical turning axis X1 is turned with the radius r about the center A of the imaging region R for the relatively small second physique P(M), and the turning support 124 can be turned while the mechanical turning axis X1 is matched with the center A of the imaging region R for the relatively large first physique P(L).

For example, when the mechanical turning axis X1 is located at or near the central position between the X-ray generator 126 and the X-ray detector 128 as in the first modification, for the relatively large first physique P(L), the turning support 124 can be turned while the mechanical turning axis X1 is fixed to the position of the center A of the imaging region R. In this case, although the degree of separation from the imaging region R of the X-ray detector 128 is larger than that in FIG. 13, the control can be performed when the magnification ratio falls within an allowable range. For the relatively small second physique P(M), the turning axis X1 is shifted to the X-ray generator side in order to bring the X-ray detector 128 closer to the imaging region R, and the turning axis X1 can be turned as described above while the state in which the turning axis X1 is disposed between the center A of the imaging region R and the X-ray generator 126 is maintained.

Second Modification

In a second modification, an example in which offset scan is performed will be described with reference to FIGS. 14 and 15. In the offset scan, a part of the imaging region R is irradiated with the X-ray while a horizontally symmetrical axes X2 of the spread of the X-ray generated from the X-ray generator 126 passes through a position deviating from the center A of the imaging region R in the imaging region R, and the X-ray generator 126 and the X-ray detector 128 turn around the imaging region R to perform the CT imaging. The X-ray irradiation range is set so as to be greater than or equal to a half of the imaging region R, and so as to be less than the whole imaging region R.

Figure 14:
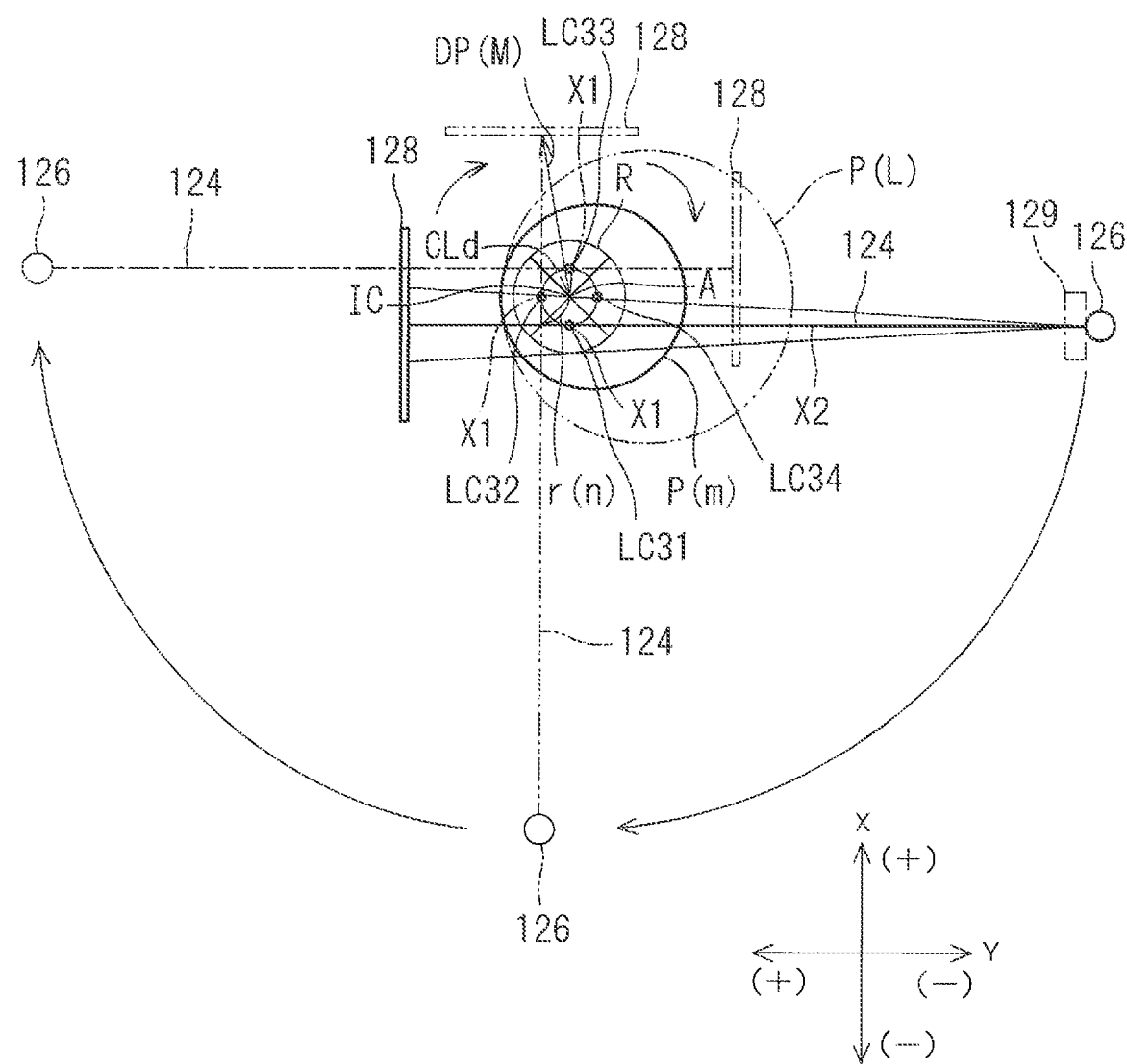
FIG. 14 is a view illustrating a turning action example when the physique is relatively small in a second modification in which offset scan is performed.
Figure 15:
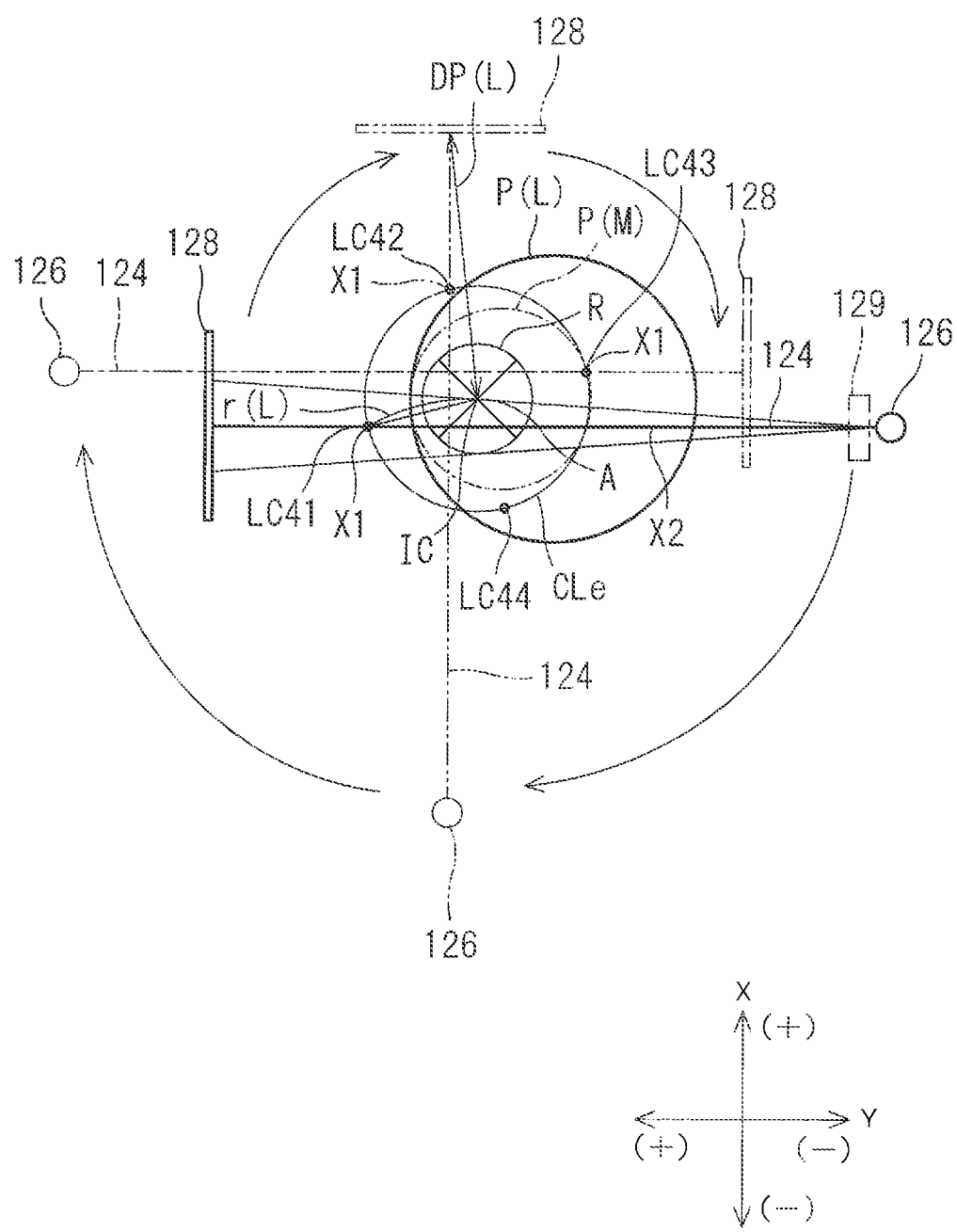
FIG. 15 is a view illustrating a turning action example when the physique is relatively large in the second modification in which the offset scan is performed.

In the example of FIGS. 14 and 15, the position of the mechanical turning axis X1 is located closer to the X-ray detector 128 than the intermediate point between the X-ray generator 126 and the X-ray detector 128 on the turning support 124.

The X-ray emitted from the X-ray generator 126 is formed into the X-ray cone beam so as to spread evenly in the width direction of the center line connecting the center of the X-ray generator 126 and the center in the width direction of the X-ray detector 128 by the X-ray regulating unit 129.

For the relatively small second physique P(M), as illustrated in FIG. 14, the mechanical turning axis X1 is disposed at a position shifted in the −x-direction with respect to the center A of the imaging region R when viewed in the xyz-orthogonal coordinate system. When viewed in the XYZ-orthogonal coordinate system, the mechanical turning axis X1 is disposed at a position shifted in the X-direction (in this case, in the −X-direction) in the initial state in FIG. 14 (the state in which the extending direction of the turning support 124 is along the X-direction). The turning support 124 is synchronously turned about the mechanical turning axis X1 while the mechanical turning axis X1 is turned with the radius r(M) about the center A of the imaging region R. That is, the mechanical turning axis X1 moves on a circular orbit CLd having the radius r(M).

In this case, when the distance of the X-ray generator 126 to the center A of the imaging region R and the distance of the X-ray detector 128 to the turning axis X1 are compared to each other, the latter is smaller, and becomes the separation distance DP(M).

The X-ray generator 126 and the X-ray detector 128 turn around the imaging turning center IC while the imaging turning center IC is placed on the position of the center A.

The mechanical turning axis X1 is located at a position LC31 shifted to the direction in which the component in the −X-direction and the component in the ±Y-direction (in the example of FIG. 14, almost zero) are combined from the center A of the imaging region R in timing when the X-ray generator 126 is located on the −Y-side while the X-ray detector 128 is located on the +Y-side, the mechanical turning axis X1 is located at a position LC32 shifted to the direction in which the component in the +Y-direction and the component in the ±X-direction (in the example of FIG. 14, almost zero) are combined from the center A of the imaging region R in timing when the X-ray generator 126 is located on the −X-side while the X-ray detector 128 is located on the +X-side, and the mechanical turning axis X1 is located at a position LC33 shifted to the direction in which the component in the +X-direction and the component in the ±Y-direction (in the example of FIG. 14, almost zero) are combined from the center A of the imaging region R in timing when the X-ray generator 126 is located on the +Y-side while the X-ray detector 128 is located on the −Y-side.

Although the X-ray generator 126 and the X-ray detector 128 are not illustrated, in timing when the X-ray generator 126 is located on the +X-side while the X-ray detector 128 is located on the −X-side, the mechanical turning axis X1 is located at a position LC34 shifted from the direction in which the component in the −Y-direction and the component in the ±X-direction (in the example in FIG. 14, almost zero) are combined from the center A of the imaging region R.

For the relatively large first physique P(L), as illustrated in FIG. 15, the mechanical turning axis X1 is disposed at a position shifted in the −x-direction and the +y-direction with respect to the center A of the imaging region R when viewed in the xyz-orthogonal coordinate system. When viewed in the XYZ-orthogonal coordinate system, the mechanical turning axis X1 is disposed at a position shifted in the X-direction (in this case, in the −X-direction) and the Y-direction (in this case, in the +Y-direction) in the initial state in FIG. 15 (the state in which the extending direction of the turning support 124 is along the X-direction). The turning support 124 is synchronously turned about the mechanical turning axis X1 while the mechanical turning axis X1 is turned with the radius r(L) (however, r(L)>r(M)) about the center A of the imaging region R. That is, the mechanical turning axis X1 moves on a circular orbit CLe having the radius r(L).

The X-ray generator 126 and the X-ray detector 128 turn around the imaging turning center IC while the imaging turning center IC is placed on the position of the center A.

The mechanical turning axis X1 is located at a position LC41 shifted to the direction in which the component in the −X-direction and the component in the +Y-direction are combined from the center A of the imaging region R in timing when the X-ray generator 126 is located on the −Y-side while the X-ray detector 128 is located on the +Y-side, the mechanical turning axis X1 is located at a position LC42 shifted to the direction in which the component in the +Y-direction and the component in the +X-direction are combined from the center A of the imaging region R in timing when the X-ray generator 126 is located on the −X-side while the X-ray detector 128 is located on the +X-side, and the mechanical turning axis X1 is located at a position LC43 shifted to the direction in which the component in the +X-direction and the component in the −Y-direction are combined from the center A of the imaging region R in timing when the X-ray generator 126 is located on the +Y-side while the X-ray detector 128 is located on the −Y-side.

Although the X-ray generator 126 and the X-ray detector 128 are not illustrated, in timing when the X-ray generator 126 is located on the +X-side while the X-ray detector 128 is located on the −X-side, the mechanical turning axis X1 is located at a position LC44 shifted to the direction in which the component in the −Y-direction and the component in the −X-direction are combined from the center A of the imaging region R.

In this case, when the distance of the X-ray generator 126 to the center A of the imaging region R and the distance of the X-ray detector 128 to the turning axis X1 are compared to each other, the latter is smaller, and becomes the separation distance DP(L).

Because of r(L)>r(M), DP(L)>DP(M) is obtained. For the relatively large first physique P(L), the X-ray generator 126 turns at a position farther from the center A of the imaging region R as compared with the relatively small second physique P(M). For this reason, the X-ray generator 126 and the X-ray detector 128 hardly contact with the head P(P1) for the relatively large first physique P(L).

Consequently, the X-ray CT imaging of the imaging region R as wide as possible can be performed by the offset scan.

Although the mechanical turning axis X1 is shifted in the −x-direction in the example of FIGS. 14 and 15, the offset scan can be performed by shifting the mechanical turning axis X1 in the +x-direction.

Unlike the second modification, the X-ray regulating unit 129 restricts the X-ray emitted from the X-ray generator 126 such that the X-ray is biased onto one side with respect to the center line connecting the center of the X-ray generator 126 and the center in the width direction of the X-ray detector 128, whereby the offset scan can be performed by the same turning action as that described in the second embodiment when the horizontal symmetry axe of the X-ray cone beam deviates from the center line and the center A of the imaging region R.

A geometrical configuration of the offset scan will be described below.

The offset scan that can be considered as an embodiment in the present application is any one of the following (A) and (B).

(A) The irradiation range of the X-ray beam is biased in the direction including the component in the +x-direction with respect to the center A of the imaging region R. The irradiation range includes the center A. A region that is not irradiated with the X-ray is generated in the −x-direction. At this point, the irradiation range is irradiated with the X-ray beam while the X-ray beam is turned by at least 360°. As a result, the whole imaging region R is irradiated with the X-ray by at least 180°, and projection data corresponding to the turning of 180° is obtained.

(B) The irradiation range of the X-ray beam is biased in the direction including the component in the −x-direction with respect to the center A of the imaging region R. The irradiation range includes the center A. A region not irradiated with the X-ray is generated in the +x-direction. At this point, the irradiation range is irradiated with the X-ray beam while the X-ray beam is turned by at least 360°. As a result, the whole imaging region R is irradiated with the X-ray by at least 180°, and projection data corresponding to the turning of 180° is obtained.

Figure 16:
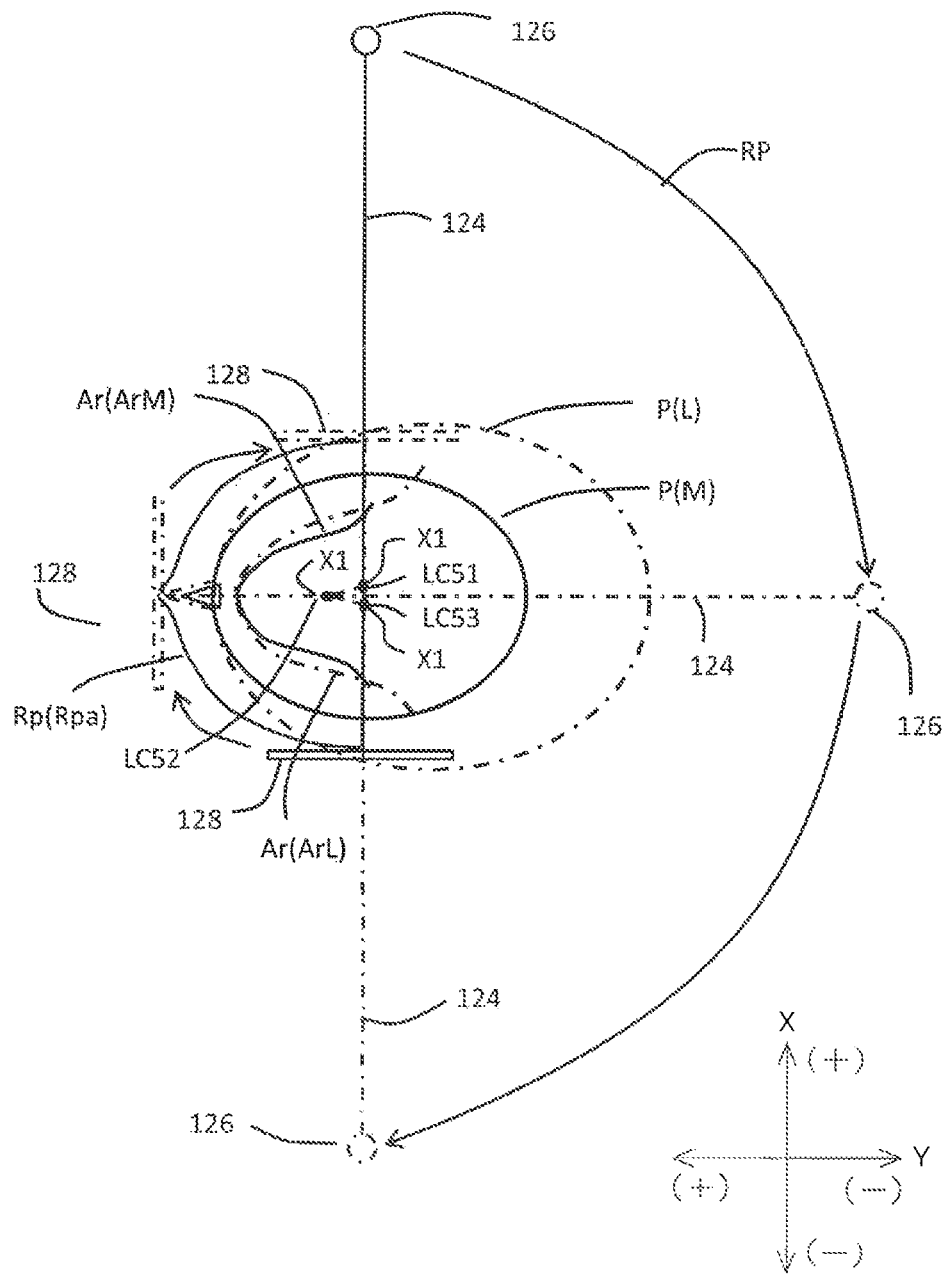
FIG. 16 is a view illustrating a turning action example when the physique is relatively small in a third modification.
Figure 17:
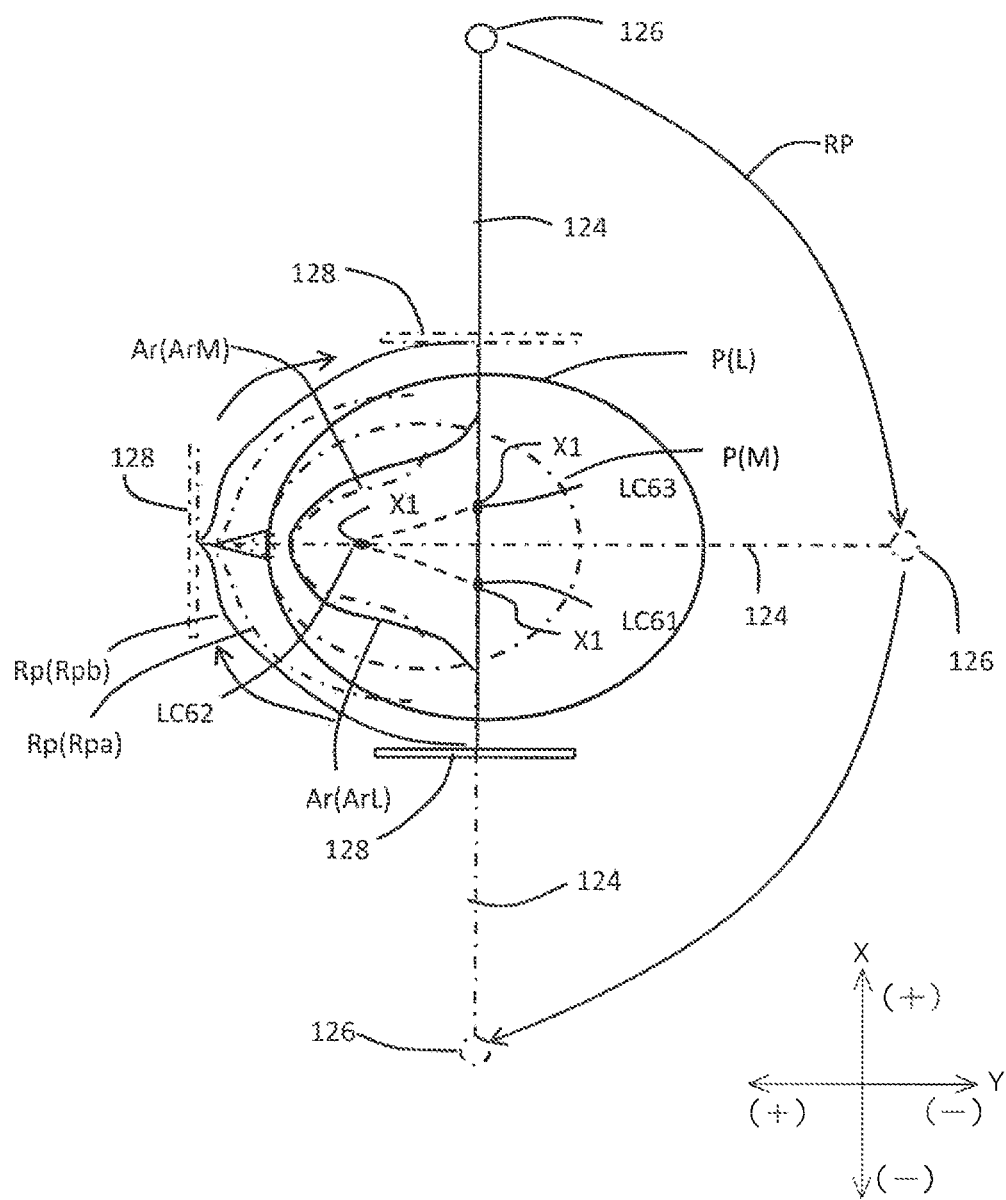
FIG. 17 is a view illustrating a turning action example when the physique is relatively large in the third modification.

In the example of FIGS. 16 and 17, the position of the mechanical turning axis X1 is shifted onto the side of the X-ray detector 128 from the intermediate point between the X-ray generator 126 and the X-ray detector 128 on the turning support 124.

Third Modification

In a third modification, an example in which panoramic X-ray imaging is performed will be described. In the panoramic X-ray imaging, as illustrated in FIG. 16, the turning support 124 is turned about the mechanical turning axis X1 under the control of the turning drive mechanism 130. Consequently, the X-ray generator 126 and the X-ray detector 128 move to perform X-ray imaging while forming a panoramic imaging orbit Rp. For example, the panoramic imaging orbit Rp is an arc-shaped trajectory along a dental arch Ar, and the X-ray generator 126 and the X-ray detector 128 move in the arc shape outside the dental arch Ar. Consequently, the X-ray panoramic image of the whole dental arch Ar can be generated.

In FIG. 16, a panoramic imaging orbit Rpa in which the relatively small second physique P(M) is assumed is set. When the panoramic imaging is performed on the relatively large first physique P(L) with the panoramic imaging orbit Rp, there is a risk that the X-ray detector 128 contacts with the head P having the physique P(L) on the outside of the molar region.

For this reason, according to the physiques P(M), P(L) of the subject set by the physique setting unit 151a, a passage route of the X-ray detector 128 is change at least in timing of irradiating a molar region Ara of the dental arch Ar with the X-ray. As this example, when the set physique of the subject is the relatively large first physique P(L), at least in timing of irradiating the molar region Ara of the dental arch Ar with the X-ray, the passage rout of the X-ray detector 128 can be set outside as compared with the case that the physique of the subject is the relatively smaller second physique P(M). Because the head P that is the subject is fixed by the head fixing apparatus 142 with the jaw as the reference, the fixed position of the front of the dental arch Ar is kept constant regardless of the physique.

As illustrated in FIG. 16, for the relatively small second physique P(M), the X-ray detector 128 is turned in the arc shape while the mechanical turning axis X1 is moved, thereby performing the panoramic X imaging.

The mechanical turning axis X1 is located at a position LC51 shifted onto the +X-side from an exact middle in the substantially same Y-coordinate as molars at right and left ends of a dental arch ArM in timing when the X-ray generator 126 is located on the +X-side while the X-ray detector 128 is located on the −X-side, the mechanical turning axis X1 is located at a position LC52 shifted onto the +Y-side from the Y-coordinate of the position LC51 on the exact middle in timing when the X-ray generator 126 is located on the −Y-side while the X-ray detector 128 is located on the +Y-side, and the mechanical turning axis X1 is located at a position LC53 shifted onto the −X-side from the exact middle in the substantially same Y-coordinate as the molars at the right and left ends of the dental arch ArM in timing when the X-ray generator 126 is located on the −X-side while the X-ray detector 128 is located on the +X-side.

On the other hand, as illustrated in FIG. 17, for the relatively large first physique P(L), the X-ray detector 128 is turned in the arc shape with a diameter larger than that in the above case while the mechanical turning axis X1 is moved, thereby performing the panoramic X imaging. Consequently, at least in timing of irradiating the molar region Ara of the dental arch Ar with the X-ray, the panoramic imaging orbit Rpb is set such that the passage route of the X-ray detector 128 is set to the outside of that in FIG. 16.

The mechanical turning axis X1 is located at a position LC61 shifted onto the −X-side from an exact middle in the substantially same Y-coordinate as molars at right and left ends of a dental arch ArL in timing when the X-ray generator 126 is located on the +X-side while the X-ray detector 128 is located on the −X-side, the mechanical turning axis X1 is located at a position LC62 shifted onto the +Y-side from the Y-coordinate of the position LC61 on the exact middle in timing when the X-ray generator 126 is located on the −Y-side while the X-ray detector 128 is located on the +Y-side, and the mechanical turning axis X1 is located at a position LC63 shifted onto the +X-side from the exact middle in the substantially same Y-coordinate as the molars at the right and left ends of the dental arch ArL in timing when the X-ray generator 126 is located on the −X-side while the X-ray detector 128 is located on the +X-side.

Because the dental arch ArL is larger than the dental arch ArM, the Y-coordinates of the positions LC61, LC63 are shifted onto the −Y-side than the Y-coordinates of the positions LC51, LC53.

Consequently, in performing the panoramic X-ray imaging, the X-ray detector 128 can be prevented from contacting with the head while brought as close as possible to the dental arch Ar according to the size of the physique.

The above configuration is applicable to an X-ray imaging apparatus that performs the panoramic X-ray imaging without assuming the above embodiment.

Fourth Modification

An example in which the subject physique setting unit automatically recognizes the physique of the subject to set the physique of the subject will be described in fourth and fifth modifications. The term "automatically recognize the physique of the subject" means that the physique is recognized based on the output of a detector such as an X-ray detector, another sensor, or the like without receiving the direct designation operation of the size of the physique. Thus, the physique of the subject can be automatically detected and set without receiving the designation operation by the operator or the like.

Figure 18:
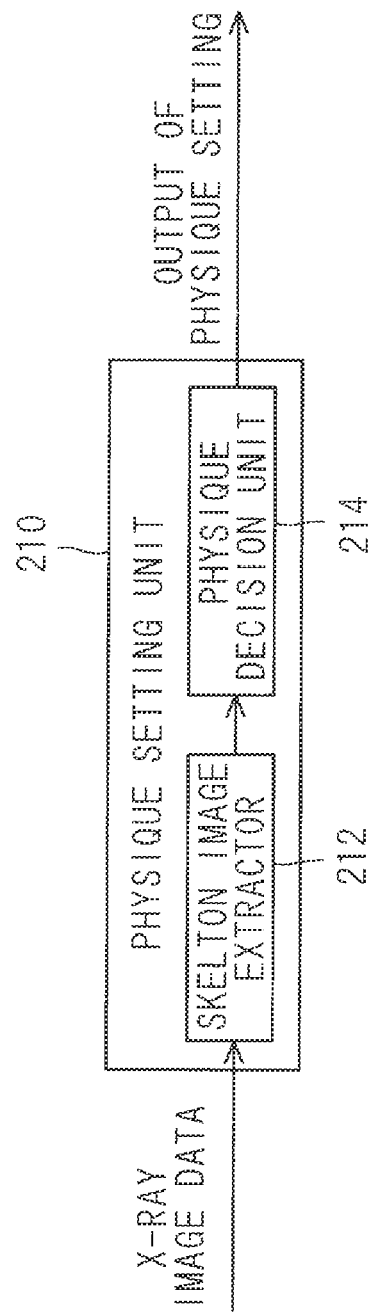
FIG. 18 is a block diagram of a fourth modification.

In the fourth modification, as illustrated in FIG. 18, a physique setting unit 210 recognizes the physique of the head P based on the captured image of the head P that is the subject, strictly the captured image data, and sets the physique based on the recognition result.

In the fourth modification, the X-ray image, more specifically a cephalographic image in FIG. 19 is used as the captured image of the head P. The cephalographic image is an image previously obtained before the X-ray CT imaging is performed using the X-ray detector 128b and the like of a cephalographic head fixing apparatus 144.

The physique setting unit 210 includes a skeleton image extractor 212 and a physique decision unit 214 that decides the size of the physique based on an extracted skeleton image.

The skeleton image extractor 212 performs binarization processing and the like based on the X-ray image and the like to extract a skeleton region of the head or a boundary region of a skeleton.

The physique decision unit 214 decides a size L of the skeleton in a predetermined operation line or the like based on the extracted skeleton region, the skeleton boundary region, or the like. The size of the physique is decided based on the decided size L of the skeleton. For example, a table in which the range of the size of the skeleton is correlated with each of the first physique P(L) or the second physique P(M) is previously stored, and whether the size L corresponds to the first physique P(L) or the second physique P(M) is decided based on the decided size L of the skeleton and the table, and the physique is set according to the decision content.

Consequently, even if the size of the physique is not particularly set, the turning control based on the size of the physique as described in the above embodiments in the X-ray generator 126 and the X-ray detector 128 can be performed based on the captured image.

Although the example in which the captured image is the cephalometric image including the entire head is described, the captured image can be the panoramic X-ray image or the X-ray image of a part of the teeth. The captured image can be an image obtained by a visible light imaging apparatus such as a typical CCD camera. The captured image can be an image captured by another X-ray imaging apparatus or a camera. Both the recognition of the X-ray image data and the recognition of the visible light captured image can be performed. In this case, one of results of the recognition of the X-ray image data and the recognition of the visible light captured image can be used to adjust the other result.

Fifth Modification

In the fifth modification, as illustrated in FIG. 20, the head fixing apparatus 142 is an example of the subject holder that holds the subject, and includes the chin rest 142a on which the jaw of the head P that is the subject can be placed and supported and the head holder 142b that holds the head P that is the subject from both outer sides of the head P. The head holder 142b is provided with a measurement unit 142c that measures the physique of the head P held by the head holder 142b. More specifically, a pair of head holders 142b is openably and closably provided so as to sandwich the left and right portions of the head P. Since the pair of head holders 142b is open and closed according to the horizontal width of the head P, an opening degree of the pair of head holders 142b becomes a size corresponding to the physique of the head P. The measurement unit 142c measures the opening degree of the pair of head holders 142b. It is assumed that the measurement unit 142c is a variable resistor in which a resistance value changes according to the opening degree of the pair of head holders 142b, an optical sensor that measures a dimension between the pair of head holders 142b, or the like. The measurement unit 142c can be called a physique measure.

The physique setting unit 251a includes the measurement unit 142c and a physique decision unit 251b. When a signal indicating the measurement result is input from the measurement unit 142c to the physique decision unit 251b, the physique decision unit 251b decides the size of the physique based on the measurement signal corresponding to the opening degree. For example, a table in which the range of the opening degree is correlated with each of the first physique P(L) or the second physique P(M) is previously stored, and whether the opening degree corresponds to the first physique P(L) or the second physique P(M) is decided based on the decided opening degree and the table, and the physique is set according to the decision content.

Consequently, the turning control based on the size of the physique as described in the above embodiments in the X-ray generator 126 and the X-ray detector 128 can be performed when the head P is fixed to the head fixing apparatus 142 even if the size of the physique is not particularly set.

Sixth Modification

Figure 21:
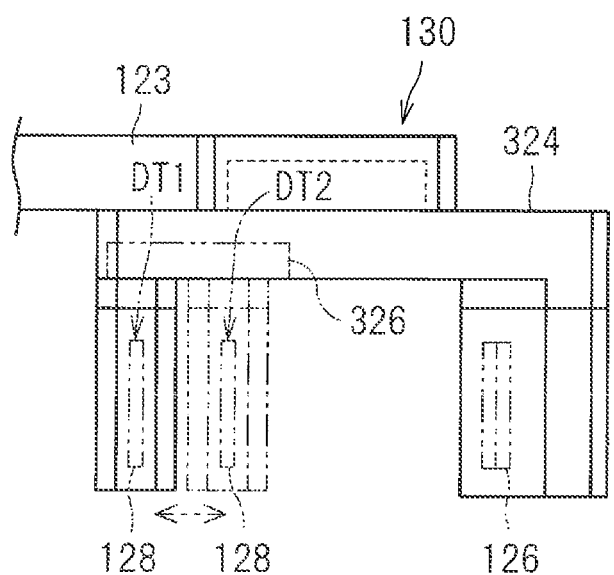
FIG. 21 is a view illustrating a turning support according to a sixth modification.

As illustrated in a sixth modification of FIG. 21, a turning support 324 can include an X-ray detector moving mechanism 326 that moves the X-ray detector 128 along the X-ray irradiation direction. The X-ray detector moving mechanism 326 is constructed with a moving mechanism including a ball screw mechanism and a motor and a linear actuator such as a linear motor. The X-ray detector moving mechanism 326 is incorporated in the turning support 324 to move the X-ray detector 128 along the extending direction of the extending direction of 324, and is displaced between a position DT1 and a position DT2. In the position DT1, the distance in the y-axis direction to the X-ray generator 126 is larger than that in the position DT2. As described above, the magnification ratio can be adjusted by moving the X-ray detector 128 along the X-ray irradiation direction. When a motor is used as a drive source of the X-ray detector moving mechanism, the motor is an X-ray detector drive motor.

Figure 22A:
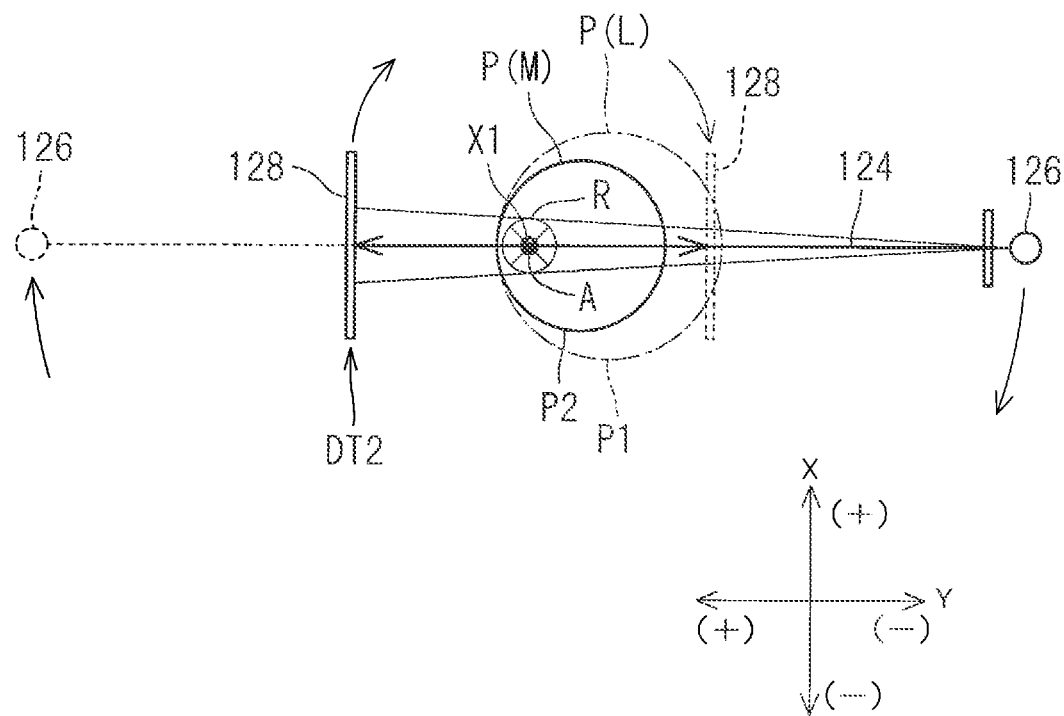
FIGS. 22A and 22B are views each illustrating a turning action example in the sixth modification.
Figure 22B:
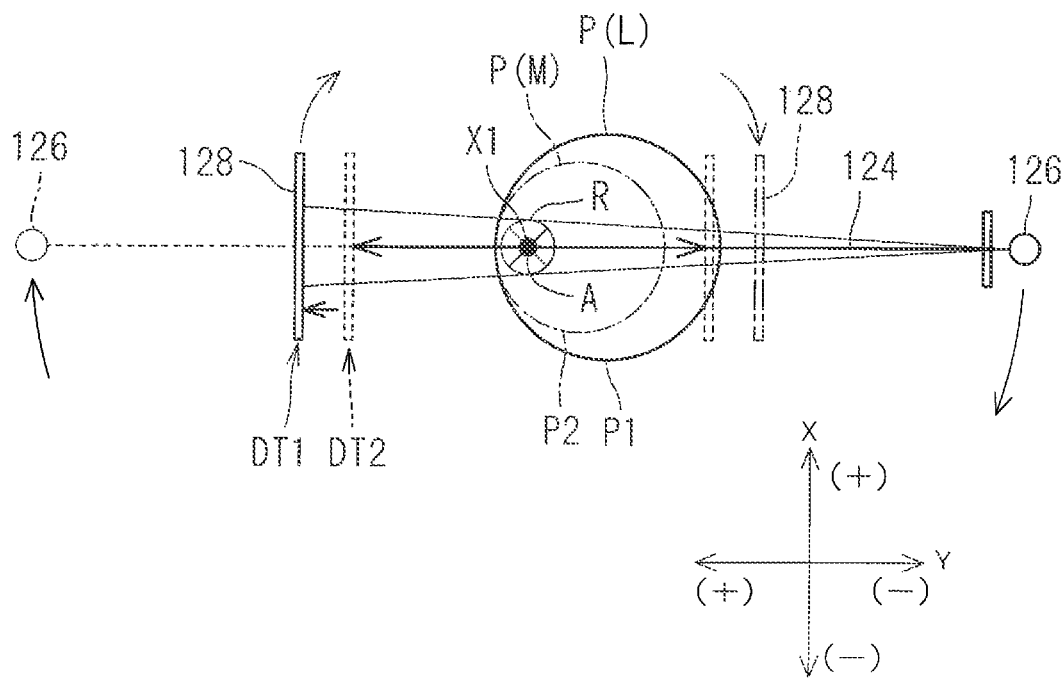

FIGS. 22A and 22B illustrate an application example of the X-ray detector moving mechanism 326 in FIG. 21.

In FIG. 22A, similarly to FIG. 10, with respect to the head P2 having the second physique P (M), CT imaging is performed with the position of the mechanical turning axis X1 aligned with the position of the center A of the imaging region R. The X-ray detector 128 is disposed at the position DT2, and does not touch with the head P2. When the turning in FIG. 22A is applied to the head P1 having the first physique P(L), there is a possibility that the X-ray detector 128 contacts with the head P1 similarly to FIG. 10.

As illustrated in FIG. 22B, with respect to the head P1, the X-ray detector 128 is displaced to the position DT1 while the mechanical turning axis X1 is fixed to the position of the center A of the imaging region R, and the turning support 324 is turned while the separation distance to the center A of the imaging region R is increased larger than the position DT2, whereby the contact of the X-ray detector 128 with the head P1 is avoided.

For this reason, even if the X-ray detector 128 is turned while the mechanical turning axis X1 is fixed to the position of the center A of the imaging region R, the X-ray detector 128 can be moved in a far and near direction with respect to the turning axis X1 according to the size of the physique. In this case, for the relatively small physique, the X-ray detector 128 is turned while located at the position DT1 relatively close to the turning axis X1, whereby the X-ray detector 128 can pass through the imaging region R as close as possible to obtain the clear image. For the relatively large physique, the X-ray detector 128 is turned while located at the position DT2 relatively far from the turning axis X1, whereby the touching of the X-ray detector 128 with the head P is avoided.

Common Modification

In each of the above embodiments and each of modifications, the X-ray generator and the X-ray detector have the circular turning orbit. Alternatively, the X-ray generator and the X-ray detector can turn while drawing an elliptical trajectory or a trajectory in which the circle and the ellipse are combined.

In each of the above embodiments and each of modifications, the turning trajectories of the X-ray generator and the X-ray detector are changed when the CT imaging is performed on the first physique and the second physique smaller than the first physique. However, the turning trajectories of the X-ray generator and the X-ray detector can be changed according to the sizes of at least three physiques. Alternatively, the turning trajectories of the X-ray generator and the X-ray detector can continuously be changed according to the setting of the continuous size of the physique. In any case, the turning trajectories of the X-ray generator and the X-ray detector can be controlled as in each of the above examples when the sizes of two physiques are assumed.

The configurations described in the above embodiments and the modifications can appropriately be combined as long as they are not inconsistent with each other.

This description also discloses the following aspects.

A first aspect is an X-ray CT imaging apparatus including: a supporter that is supported such that an X-ray generator and an X-ray detector are opposed to each other with a subject sandwiched between the X-ray generator and the X-ray detector; a turning motor that turns the supporter about a shaft located between the X-ray generator and the X-ray detector; a crosswise drive motor that moves the shaft in a crosswise direction, an axial direction of the shaft being set to a longitudinal direction, a direction intersecting with the longitudinal direction being set to the crosswise direction; and a circuit that performs processing of controlling the turning motor and the crosswise drive motor and processing of setting a physique of the subject from physique data of the subject. When X-ray CT imaging is performed by irradiating the subject with an X-ray generated from the X-ray generator, the crosswise drive motor moves the shaft in synchronization with turning of the supporter about the shaft using the turning motor, and the supporter is caused to perform combined motion, which allows the X-ray generator and the X-ray detector to turn about a center of an X-ray CT imaging region, and position control of the shaft is performed according to a size of the physique of the subject.

A second aspect that is the first aspect is the X-ray CT imaging apparatus in which the circuit switches between drive control in which the supporter is caused to perform the combined motion and drive control in which the supporter is turned while the shaft is fixed to a position of the center of the X-ray CT imaging region, according to the size of the physique of the subject.

A third aspect that is the first or second aspect is the X-ray CT imaging apparatus in which, according to the size of the physique of the subject set, the circuit performs the drive control in which the supporter is caused to perform the combined motion when the set physique of the subject is a first physique, and the circuit performs the drive control in which the supporter is turned while the shaft is fixed to a position of the center of the X-ray CT imaging region when the set physique of the subject is a second physique smaller than the first physique.

A fourth aspect that is any one of the first to third aspects is the X-ray CT imaging apparatus in which a distance of the shaft to the center of the X-ray CT imaging region is changed according to the set size of the physique of the subject when the combined motion is performed by the supporter.

A fifth aspect that is any one of the first to fourth aspects is the X-ray CT imaging apparatus in which, when the X-ray generator and the X-ray detector are turned around the center of the X-ray CT imaging region, assuming that a separation distance is smaller one of a distance between the center of the X-ray CT imaging region and the X-ray generator and a distance between the center of the X-ray CT imaging region and the X-ray detector, a position of the shaft with respect to the center of the X-ray CT imaging region is controlled such that the separation distance when the physique of the subject is the first physique is larger than the separation distance when the physique of the subject is the second physique smaller than the first physique according to the size of the physique of the subject.

A sixth aspect that is any one of the first to fifth aspects is the X-ray CT imaging apparatus in which, when the supporter is caused to perform the combined motion, the crosswise drive motor rotates the shaft about the center of the X-ray CT imaging region in synchronization with the turning of the supporter about the shaft using the turning motor.

A seventh aspect that is any one of the first to sixth aspects is the X-ray CT imaging apparatus in which the circuit controls adjustment of a regulation amount of the X-ray generated from the X-ray generator according to a distance of the X-ray generator to the center of the X-ray CT imaging region when the X-ray generator and the X-ray detector are turned about the center of the X-ray CT imaging region.

An eighth aspect that is any one of the first to seventh aspects is the X-ray CT imaging apparatus in which the shaft is disposed along a vertical direction.

A ninth aspect that is any one of the first to eighth aspects is the X-ray CT imaging apparatus in which the X-ray CT imaging is performed with a jaw region of a head of the subject as the X-ray CT imaging region.

A tenth aspect that is the ninth aspect is the X-ray CT imaging apparatus in which the X-ray CT imaging is performed with a part of a dental arch on the head of the subject as the X-ray CT imaging region.

An eleventh aspect that is any one of the first to tenth aspects is the X-ray CT imaging apparatus in which the X-ray generator and the X-ray detector turn around the X-ray CT imaging region to perform the X-ray CT imaging by offset scan while a part of the X-ray CT imaging region is irradiated with the X-ray generated from the X-ray generator at a position where a symmetrical axis of spread of the X-ray deviates from the center of the X-ray CT imaging region.

A twelfth aspect that is any one of the first to eleventh aspects is the X-ray CT imaging apparatus in which the circuit performs the control in which a distance of the X-ray generator to the center of the X-ray CT imaging region and a distance of the X-ray detector to the center of the X-ray CT imaging region are kept constant while the X-ray CT imaging is performed by irradiating the subject with the X-ray generated from the X-ray generator.

A thirteenth aspect that is any one of the first to twelfth aspects is the X-ray CT imaging apparatus in which the circuit sets the physique of the subject through reception of an input operation of the physique of the subject.

A fourteenth aspect that is the thirteenth aspect is the X-ray CT imaging apparatus in which the circuit sets the physique by receiving an input operation to select one of physique sizes of a plurality of selection candidates.

A fifteenth aspect that is any one of the first to the twelfth aspects is the X-ray CT imaging apparatus in which the circuit automatically recognizes the physique of the subject from at least one of data of a captured image obtained by performing X-ray imaging of the subject or data of a captured image obtained by performing visible light imaging of the subject, and sets the physique of the subject.

A sixteenth aspect that is any one of the first to twelfth aspects is the X-ray CT imaging apparatus including a subject holder that holds the subject and a physique measure that is provided in the subject holder to measure the physique of the subject held by the subject holder. The physique of the subject is set based on a measurement result of the physical measure.

A seventeenth aspect that is any one of the first to sixteenth aspects is the X-ray CT imaging apparatus in which the supporter includes an X-ray detector drive motor that moves the X-ray detector along an X-ray irradiation direction.

An eighteenth aspect that is any one of the first to seventeenth aspects is the X-ray CT imaging apparatus in which the crosswise drive motor is controlled such that the X-ray generator and the X-ray detector form a panoramic imaging orbit to perform panoramic X-ray imaging of a dental arch of the subject, and a passage route of the X-ray detector is changed at least in timing of irradiating to a molar region of the dental arch with the X-ray according to the size of the physique of the subject set by the circuit.

Further, this application discloses the following aspects. According to a first aspect of the present disclosure, an X-ray CT imaging apparatus includes: a turning support that supports an X-ray generator and an X-ray detector so that the X-ray generator and the X-ray detector are opposed to each other with a subject sandwiched therebetween; a turning drive mechanism including a turning mechanism that turns the turning support about a mechanical turning axis located between the X-ray generator and the X-ray detector and a turning axis moving mechanism that moves the mechanical turning axis in a direction intersecting with an axial direction of the mechanical turning axis; a subject physique setting unit that can set a size of a physique of the subject; and a turning controller that controls the turning mechanism and the turning axis moving mechanism. When X-ray CT imaging is performed by irradiating the subject with an X-ray generated from the X-ray generator, the turning axis moving mechanism moves the mechanical turning axis in synchronization with turning of the turning support about the mechanical turning axis using the turning mechanism, and the turning support is caused to perform combined motion, which allows the X-ray generator and the X-ray detector to turn about a center of an X-ray CT imaging region, and position control of the turning axis is performed according to a size of the physique of the subject set by the subject physique setting unit.

In a second aspect that is the X-ray CT imaging apparatus of the first aspect, drive control in which the turning support is caused to perform the combined motion and drive control in which the turning support is turned while the mechanical turning axis is fixed to a position of the center of the X-ray CT imaging region are switched according to the size of the physique of the subject set by the subject physique setting unit.

In a third aspect that is the X-ray CT imaging apparatus of the second aspect, according to the size of the physique of the subject set by the subject physique setting unit, the drive control in which the turning support is caused to perform the combined motion is performed when the set physique of the subject is a first physique, and the drive control in which the turning support is turned while the mechanical turning axis is fixed to a position of the center of the X-ray CT imaging region is performed when the set physique of the subject is a second physique smaller than the first physique.

In a fourth aspect that is the X-ray CT imaging apparatus of any one of the first to third aspects, a distance of the mechanical turning axis to the center of the X-ray CT imaging region is changed according to the size of the physique of the subject set by the subject physique setting unit when the turning support is caused to perform the combined motion.

In a fifth aspect that is the X-ray CT imaging apparatus of any one of the first to fourth aspects, when the X-ray generator and the X-ray detector are turned about the center of the X-ray CT imaging region, assuming that a separation distance is smaller one of a distance between the center of the X-ray CT imaging region and the X-ray generator and a distance between the center of the X-ray CT imaging region and the X-ray detector, a position of the mechanical turning axis with respect to the center of the X-ray CT imaging region is controlled such that the separation distance when the set physique of the subject is the first physique is larger than the separation distance when the set physique of the subject is the second physique smaller than the first physique according to the size of the physique of the subject set by the subject physique setting unit.

In a sixth aspect that is the X-ray CT imaging apparatus of any one of the first to fifth aspects, when the turning support is caused to perform the combined motion, the turning axis moving mechanism rotates the mechanical turning axis about the center of the X-ray CT imaging region in synchronization with the turning of the turning support about the mechanical turning axis using the turning mechanism.

A seventh aspect that is the X-ray CT imaging apparatus of any one of the first to sixth aspects further includes an X-ray regulating unit that adjusts a regulation amount of the X-ray generated from the X-ray generator according to a distance of the X-ray generator to the center of the X-ray CT imaging region when the X-ray generator and the X-ray detector are turned about the center of the X-ray CT imaging region.

In an eighth aspect that is the X-ray CT imaging apparatus of any one of the first to seventh aspects, the mechanical turning axis is disposed along a vertical direction.

In a ninth aspect that is the X-ray CT imaging apparatus of any one of the first to eighth aspects, the X-ray CT imaging is performed with a jaw region of a head of the subject as the X-ray CT imaging region.

In a tenth aspect that is the X-ray CT imaging apparatus of the ninth aspect, the X-ray CT imaging is performed with a part of a dental arch of the head of the subject as the X-ray CT imaging region.

In an eleventh aspect that is the X-ray CT imaging apparatus of any one of the first to tenth aspects, the X-ray generator and the X-ray detector turn around the X-ray CT imaging region to perform the X-ray CT imaging by offset scan while a part of the X-ray CT imaging region is irradiated with the X-ray generated from the X-ray generator at a position where a symmetrical axis of spread of the X-ray deviates from the center of the X-ray CT imaging region.

In a twelfth aspect that is the X-ray CT imaging apparatus of any one of the first to eleventh aspects, a distance of the X-ray generator to the center of the X-ray CT imaging region and a distance of the X-ray detector to the center of the X-ray CT imaging region are kept constant while the X-ray CT imaging is performed by irradiating the subject with the X-ray generated from the X-ray generator.

In a thirteenth aspect that is the X-ray CT imaging apparatus of any one of the first to twelfth aspects, the subject physique setting unit sets the physique of the subject by receiving an input operation of the physique of the subject.

In a fourteenth aspect that is the X-ray CT imaging apparatus of the thirteenth aspect, the subject physique setting unit sets the physique by receiving an input operation to select one of physique sizes of a plurality of selection candidates.

In a fifteenth aspect that is the X-ray CT imaging apparatus of any one of the first to twelfth aspects, the subject physique setting unit sets the physique of the subject by automatically recognizing the physique of the subject.

In a sixteenth aspect that is the X-ray CT imaging apparatus of the fifteenth aspect, the subject physique setting unit recognizes the physique of the subject based on a captured image of the subject, and sets the physique based on a recognition result.

In a seventeenth aspect that is the X-ray CT imaging apparatus of the fifteenth aspect, the subject physique setting unit includes a measurement unit that is provided in a holder that holds the subject, and measures the physique of the subject held by the holder, and the subject physique setting unit sets the physique of the subject based on a measurement result of the measurement unit.

In an eighteenth aspect that is the X-ray CT imaging apparatus of the seventeenth aspect, the measurement unit measures an opening degree of a plurality of members that hold the subject.

In a nineteenth aspect that is the X-ray CT imaging apparatus of any one of the first to eighteenth aspects, the turning support includes an X-ray detector moving mechanism that moves the X-ray detector along an X-ray irradiation direction.

In a twentieth aspect that is the X-ray CT imaging apparatus of any one of the first to nineteenth aspects, the turning drive mechanism is controlled such that the X-ray generator and the X-ray detector form a panoramic imaging orbit to perform panoramic X-ray imaging of a dental arch of the subject, and a passage route of the X-ray detector is changed at least in timing of irradiating to a molar region of the dental arch with the X-ray according to the size of the physique of the subject.

In the X-ray CT imaging apparatus of the first aspect, the position control of the turning axis is performed according to the size of the physique of the subject set by the subject physique setting unit. Consequently, the orbits on which the X-ray generator and the X-ray detector turn can be changed to prevent the X-ray generator and the X-ray detector that turn around the subject from contacting with the subject.

In the second aspect, the orbit on which the X-ray generator and the X-ray detector turn can be changed according to the size of the physique of the subject by switching the drive control in which the turning support is caused to perform the combined motion and the drive control in which the turning support is turned while the mechanical turning axis is fixed to a position of the center of the X-ray CT imaging region according to the size of the physique of the subject set by the subject physique setting unit.

In the third aspect, when the set physique of the subject is the relatively small second physique, the turning support is turned while the mechanical turning axis is fixed to the center position of the X-ray CT imaging region, so that the position of the mechanical turning axis is stabilized to easily obtain a clear X-ray CT image. When the set physique of the subject is the relatively large first physique, the turning support is caused to perform combined motion, the X-ray generator and the X-ray detector that turn around the subject can be prevented from contacting with the subject by causing the turning support to perform the combined motion.

In the fourth aspect, when the turning support is caused to perform the combined motion, the distance of the mechanical turning axis to the center of the X-ray CT imaging region is changed according to the size of the physique of the subject set by the subject physique setting unit, which allows the orbit on which the X-ray generator and the X-ray detector turn to be changed according to the size of the physique of the subject In the fifth aspect, when the X-ray generator and the X-ray detector are turned about the center of the X-ray CT imaging region, assuming that a separation distance is smaller one of a distance between the center of the X-ray CT imaging region and the X-ray generator and a distance between the center of the X-ray CT imaging region and the X-ray detector, the position of the mechanical turning axis with respect to the center of the X-ray CT imaging region is controlled such that the separation distance when the set physique of the subject is the first physique is larger than the separation distance when the set physique of the subject is the second physique smaller than the first physique according to the size of the physique of the subject set by the subject physique setting unit, which allows the X-ray generator and the X-ray detector turn around the subject to be prevented from contacting with the subject.

In the sixth aspect, when the turning support is caused to perform the combined motion, the turning axis moving mechanism rotates the mechanical turning axis about the center of the X-ray CT imaging region in synchronization with the turning of the turning support about the mechanical turning axis using the turning mechanism, which allows the X-ray generator and the X-ray detector to turn along the orbit as close as to the circle.

In the seventh aspect, the adjustment can be performed according to the distance of the X-ray generator to the center of the X-ray CT imaging region such that an appropriate amount of X-ray is incident on the X-ray CT imaging region.

In the eighth aspect, the X-ray generator and the X-ray detector can be turned around the axis along the vertical direction.

In the ninth aspect, when the X-ray CT imaging is performed on the jaw region, the X-ray generator and the X-ray detector can be prevented from contacting with the head according to the physique of the head of the subject.

In the tenth aspect, when the X-ray CT imaging is performed on a part of the dental arch, the X-ray generator and the X-ray detector can be prevented from contacting with the head according to the physique of the head of the subject.

In the eleventh aspect, the X-ray CT imaging of the X-ray CT imaging region as wide as possible can be performed by offset scan.

In the twelfth aspect, the X-ray CT imaging can be performed while the magnification ratio is kept constant.

In the thirteenth aspect, when the operator or the like of the apparatus performs the input operation, which allows the setting of the physique of the subject.

In the fourteenth aspect, the operator or the like of the apparatus can easily perform the input operation by selecting one of the physique sizes of the plurality of selection candidates.

In the fifteenth aspect, the physique of the subject can be automatically detected and set.

In the sixteenth aspect, the physique of the subject can be automatically detected and set based on the captured image.

In the seventeenth aspect, the physique of the subject can automatically be set when the subject is held by the holder.

In the eighteenth aspect, the physique of the subject can be set based on the opening degrees of the plurality of members that hold the subject.

In the nineteenth aspect, the magnification ratio can be adjusted by moving the X-ray detector along the X-ray irradiation direction.

In the twentieth aspect, the X-ray generator can be prevented from contacting with the head when the panoramic imaging is performed.

Although the present disclosure is described in detail, the above description is illustrative in all aspects, but the disclosure is not limited thereto.

Innumerable modifications not illustrated can be envisaged without departing from the scope of the present disclosure.

EXPLANATION OF REFERENCE SIGNS 10, 110: X-ray CT imaging apparatus
20, 124, 324: turning support
22, 126: X-ray generator
24, 128: X-ray detector
30, 130: turning drive mechanism
32, 132: turning mechanism
38, 134: turning axis moving mechanism
40: subject physique setting unit
60: turning controller
129: X-ray regulating unit
142: head fixing apparatus
142b: head holder
142c: measurement unit
150: main body controller
151a: physique setting unit
151b: turning controller
153a: imaging program
153b: reference table
158: operation panel apparatus
158a: display
158b: touch detector
193: physique setting image
193a: normal-size selection image
193b: large-size selection image
210, 251a: physique setting unit
212: skeleton image extractor
214, 251b: physique decision unit
326: X-ray detector moving mechanism
A: center of imaging region
Ar: dental arch
P: subject (head)
P(L): first physique
P(M): second physique
R: imaging region
Rp: panoramic imaging orbit
X1: mechanical turning axis

What is claimed is:
1. An X-ray CT imaging apparatus comprising:
a supporter supported such that an X-ray generator and an X-ray detector are opposed to each other with a subject sandwiched between the X-ray generator and the X-ray detector;
a turning motor configured to turn said supporter about a shaft located between said X-ray generator and the X-ray detector;
a crosswise drive motor configured to move said shaft in a crosswise direction, a direction parallel to an axial direction of said shaft being set to a longitudinal direction, a direction intersecting with said longitudinal direction being set to said crosswise direction; and
a circuit configured to perform processing of controlling said turning motor and said crosswise drive motor and processing of setting a physique of said subject from physique data of the subject,
wherein when X-ray CT imaging is performed by irradiating the subject with an X-ray generated from said X-ray generator, said crosswise drive motor moves said shaft in synchronization with turning of said supporter about said shaft using said turning motor, and said supporter is caused to perform combined motion, which allows said X-ray generator and said X-ray detector to turn about a center of an X-ray CT imaging region, and position control of said shaft is performed according to a size of the physique of said subject.
2. The X-ray CT imaging apparatus according to claim 1, wherein said circuit is further configured to switch between drive control in which said supporter is caused to perform said combined motion and drive control in which said supporter is turned while said shaft is fixed to a position of the center of said X-ray CT imaging region, according to the size of the physique of said subject.

3. The X-ray CT imaging apparatus according to claim 1, wherein, according to the size of the physique, said circuit is further configured to perform drive control in which said supporter is caused to perform said combined motion when a set physique of the subject is a first physique, and said circuit is further configured to perform drive control in which said supporter is turned while said shaft is fixed to a position of the center of said X-ray CT imaging region when the set physique of said subject is a second physique smaller than said first physique.

4. The X-ray CT imaging apparatus according to claim 1, wherein a distance of said shaft to the center of said X-ray CT imaging region is changed according to a set size of the physique of said subject when said combined motion is performed by said supporter.

5. The X-ray CT imaging apparatus according to claim 1, wherein, when said X-ray generator and said X-ray detector are turned around the center of said X-ray CT imaging region, assuming that a separation distance is smaller one of a distance between the center of said X-ray CT imaging region and said X-ray generator and a distance between the center of said X-ray CT imaging region and said X-ray detector, a position of said shaft with respect to the center of said X-ray CT imaging region is controlled such that said separation distance when the physique of said subject is a first physique is larger than said separation distance when the physique of said subject is a second physique smaller than the first physique according to the size of the physique of said subject.

6. The X-ray CT imaging apparatus according to claim 1, wherein, when said supporter is caused to perform said combined motion, said crosswise drive motor rotates said shaft about the center of said X-ray CT imaging region in synchronization with the turning of said supporter about said shaft using said turning motor.

7. The X-ray CT imaging apparatus according to claim 1, wherein said circuit is further configured to control adjustment of a regulation amount of the X-ray generated from said X-ray generator according to a distance of said X-ray generator to the center of said X-ray CT imaging region when said X-ray generator and said X-ray detector are turned about the center of said X-ray CT imaging region.

8. The X-ray CT imaging apparatus according to claim 1, wherein said shaft is disposed along a vertical direction.

9. The X-ray CT imaging apparatus according to claim 1, wherein the X-ray CT imaging is performed with a jaw region of a head of the subject as said X-ray CT imaging region.

10. The X-ray CT imaging apparatus according to claim 9, wherein the X-ray CT imaging is performed with a part of a dental arch of the head of the subject as said X-ray CT imaging region.

11. The X-ray CT imaging apparatus according to claim 1, wherein said X-ray generator and said X-ray detector turn around said X-ray CT imaging region to perform the X-ray CT imaging by offset scan while a part of said X-ray CT imaging region is irradiated with said X-ray generated from said X-ray generator at a position where a symmetrical axis of spread of said X-ray deviates from the center of said X-ray CT imaging region.

12. The X-ray CT imaging apparatus according to claim 1, wherein said circuit is further configured to perform control in which a distance of said X-ray generator to the center of said X-ray CT imaging region and a distance of said X-ray detector to the center of said X-ray CT imaging region are kept constant while the X-ray CT imaging is performed by irradiating the subject with the X-ray generated from said X-ray generator.

13. The X-ray CT imaging apparatus according to claim 1, wherein said circuit is further configured to set the physique of said subject through reception of an input operation of the physique of the subject.

14. The X-ray CT imaging apparatus according to claim 1, wherein said circuit is further configured to set the physique by receiving an input operation to select one of physique sizes of a plurality of selection candidates.

15. The X-ray CT imaging apparatus according to claim 1, wherein said circuit is further configured to automatically recognize the physique of the subject from at least one of data of a captured image obtained by performing X-ray imaging of said subject or data of a captured image obtained by performing visible light imaging of said subject, and set the physique of said subject.

16. The X-ray CT imaging apparatus according to claim 1, further comprising:
 a subject holder configured to hold said subject; and
 a physique measure provided in said subject holder to measure the physique of
 the subject held by said subject holder,
 wherein the physique of the subject is set based on a measurement result of said physical measure.

17. The X-ray CT imaging apparatus according to claim 1, wherein said supporter includes an X-ray detector drive motor configured to move said X-ray detector along an X-ray irradiation direction.

18. The X-ray CT imaging apparatus according to claim 1, wherein said crosswise drive motor is controlled such that said X-ray generator and said X-ray detector form a panoramic imaging orbit to perform panoramic X-ray imaging of a dental arch of the subject, and a passage route of said X-ray detector is changed at least at timing of irradiating to a molar region of said dental arch with the X-ray according to the size of the physique of the subject set by said circuit.

* * * * *